US008231268B2

(12) United States Patent
Krol et al.

(10) Patent No.: US 8,231,268 B2
(45) Date of Patent: Jul. 31, 2012

(54) SCREENING SYSTEM AND METHOD FOR ANALYZING A PLURALITY OF BIOSENSORS

(75) Inventors: Mark F. Krol, Painted Post, NY (US); Thomas C. Moore, Jena (DE); David A. Pastel, Horseheads, NY (US); Gordon M. Shedd, Lawrenceville, PA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/034,214

(22) Filed: Feb. 24, 2011

(65) Prior Publication Data

US 2011/0142092 A1    Jun. 16, 2011

Related U.S. Application Data

(62) Division of application No. 11/521,771, filed on Sep. 15, 2006, now Pat. No. 7,976,217.

(51) Int. Cl.
*G01K 3/00*    (2006.01)
*G01K 7/00*    (2006.01)
*G01K 11/00*   (2006.01)
*G01K 1/00*    (2006.01)

(52) U.S. Cl. ........ 374/137; 374/110; 374/166; 374/120; 374/141

(58) Field of Classification Search ................. 374/137, 374/166, 110, 120, 141
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 4,952,056 A | 8/1990 | Tiefenthaler | 356/73.1 |
| 5,262,842 A | 11/1993 | Gauglitz et al. | 356/345 |
| 5,313,264 A | 5/1994 | Ivarsson et al. | 356/73 |
| 5,459,300 A | 10/1995 | Kasman | 219/433 |
| 5,470,744 A | 11/1995 | Astle | 435/286.7 |
| 5,738,825 A | 4/1998 | Rudigier et al. | 422/82.11 |
| 6,018,388 A | 1/2000 | Nawracala et al. | 356/246 |
| 6,129,428 A | 10/2000 | Helwig et al. | 312/114 |
| 6,200,814 B1 | 3/2001 | Malmqvist et al. | 436/52 |
| 6,395,558 B1 | 5/2002 | Duveneck et al. | 436/172 |
| 6,455,004 B1 | 9/2002 | Tiefenthaler | 422/91 |
| 6,478,524 B1 | 11/2002 | Malin | 414/283 |
| 6,710,877 B2 | 3/2004 | Chase et al. | 356/432 |
| 6,721,053 B1 | 4/2004 | Maseeh | 356/436 |
| 6,767,607 B2 | 7/2004 | Tanner et al. | 428/131 |

(Continued)

FOREIGN PATENT DOCUMENTS

EP    0 570 445    8/1996

(Continued)

OTHER PUBLICATIONS

A.J. Pope et al., "Homogeneous fluorescence readouts for miniaturized high-throughput screening: theory and practice", Drug Discovery Today, vol. 4, No. 8, Aug. 1999, pp. 350-362.

(Continued)

*Primary Examiner* — Lisa Caputo
*Assistant Examiner* — Mirellys Jagan
(74) *Attorney, Agent, or Firm* — Gregory B. Butler

(57) ABSTRACT

A screening device and a method are described herein which can automatically handle and measure (interrogate) a plurality of sensor carriers (i.e., multiwell plates, microplates) with multi-dimensionally arranged, temperature-compensated or temperature-compensatable optical sensors, while maintaining a substantially constant temperature gradient for a relatively long period of time around the optical sensors where temperature compensation has been performed on the sensor carriers.

3 Claims, 21 Drawing Sheets

U.S. PATENT DOCUMENTS

| | | | |
|---|---|---|---|
| 6,785,433 B2 | 8/2004 | Tiefenthaler | 385/12 |
| 6,787,110 B2 | 9/2004 | Tiefenthaler | 422/91 |
| 6,818,886 B2 | 11/2004 | Tiefenthaler | 250/282 |
| 6,829,073 B1 | 12/2004 | Krol et al. | 359/263 |
| 6,958,131 B2 | 10/2005 | Tiefenthaler | 422/82.05 |
| 6,985,664 B2 | 1/2006 | Caracci et al. | 385/130 |
| 7,057,720 B2 | 6/2006 | Caracci et al. | 356/300 |
| 7,081,600 B2 * | 7/2006 | Brown et al. | 219/428 |
| 7,136,550 B2 | 11/2006 | Mozdy | 385/28 |
| 2001/0055817 A1 | 12/2001 | Malmqvist et al. | 436/531 |
| 2002/0098592 A1 * | 7/2002 | Neilson et al. | 436/147 |
| 2002/0127565 A1 | 9/2002 | Cunningham et al. | 435/6 |
| 2002/0168295 A1 | 11/2002 | Cunningham et al. | 422/82.05 |
| 2003/0003018 A1 | 1/2003 | Stolowitz et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0031829 A1 | 2/2003 | Tanner et al. | 428/131 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2003/0118078 A1 * | 6/2003 | Carlson et al. | 374/160 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0191765 A1 | 9/2004 | Mozdy et al. | 435/5 |
| 2004/0223881 A1 | 11/2004 | Cunningham et al. | 422/82.05 |
| 2004/0247486 A1 | 12/2004 | Tiefenthaler | 422/82.11 |
| 2004/0258568 A1 | 12/2004 | Lutz et al. | 422/99 |
| 2005/0070027 A1 | 3/2005 | Gollier et al. | 436/518 |
| 2005/0099622 A1 | 5/2005 | Caracci et al. | 356/300 |
| 2005/0170498 A1 | 8/2005 | Dolley et al. | 435/288.4 |
| 2005/0236554 A1 | 10/2005 | Fontaine et al. | 250/208.1 |
| 2005/0264818 A1 | 12/2005 | Gollier | 356/445 |
| 2006/0062509 A1 | 3/2006 | Krol et al. | 385/12 |
| 2006/0106557 A1 | 5/2006 | Fontaine et al. | 702/87 |
| 2006/0110594 A1 | 5/2006 | Frutos et al. | 428/332 |
| 2006/0139641 A1 | 6/2006 | Gollier et al. | 356/399 |
| 2006/0141527 A1 | 6/2006 | Caracci et al. | 435/7.1 |
| 2006/0141611 A1 | 6/2006 | Frutos et al. | 435/287.2 |
| 2006/0146317 A1 | 7/2006 | Aklian | 356/128 |
| 2006/0180750 A1 | 8/2006 | Gollier et al. | 250/227.11 |
| 2006/0182382 A1 | 8/2006 | Gollier et al. | 385/12 |
| 2006/0223051 A1 | 10/2006 | Fang et al. | 435/4 |
| 2006/0229818 A1 | 10/2006 | Fang et al. | 702/19 |

FOREIGN PATENT DOCUMENTS

| | | |
|---|---|---|
| EP | 0 660 924 | 9/1999 |
| WO | WO 90/05295 | 5/1990 |
| WO | WO 95/22754 | 8/1995 |
| WO | WO 98/09156 | 3/1998 |
| WO | WO 99/09392 | 2/1999 |
| WO | WO 02/079761 | 10/2002 |

OTHER PUBLICATIONS

M.A. Sills et al., "Comparison of Assay Technologies for a Tyrosine Kinase Assay Generates Different Results in HTS", Journal of Biomolecular Screening, vol. 7, 2002, pp. 191.

J. Comley, "Label-Free Detection—New Biosensors Facilitate Broader Range of Drug Discovery Application", Drug Discovery World, Winter 2004, vol. 5, pp. 63-74.

M.A. Cooper, "Current biosensor technologies in drug discovery", Drug Discovery World Summer 2006, pp. 68-82.

J. Comley, "New Options for Cell-Based Assay Automation", Drug Discovery World Fal 2005, pp. 39-62.

C. Eggeling et al., "Highly sensitive fluorescence detection technology currently available for HTS", DDT, vol. 8, No. 14, Jul. 2003, pp. 632-641.

J.R. Denmark et al., "Standardization of enzyme-linked immunosorbent assay (ELISA) and the detection of Toxoplasma antibody", Medical Laboratory Science, 1978, vol. 35, pp. 227-232.

"Working Group Updates", Journal of Biomolecular Screening, vol. 1, No. 4, 1996, pp. 163-168.

* cited by examiner

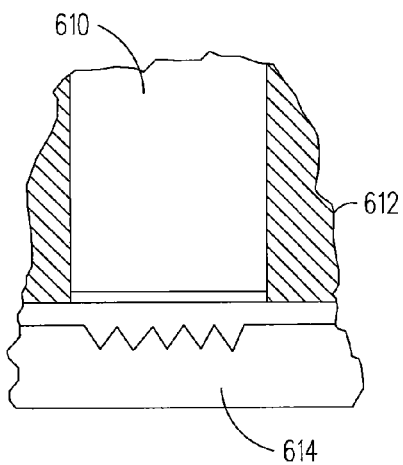 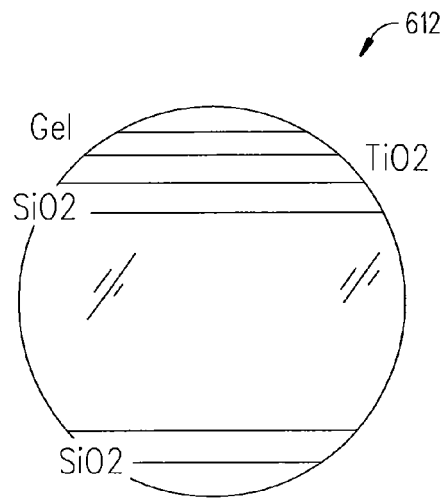
FIG. 6C    FIG. 6D
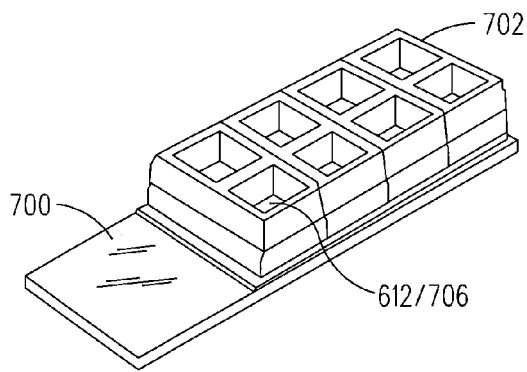 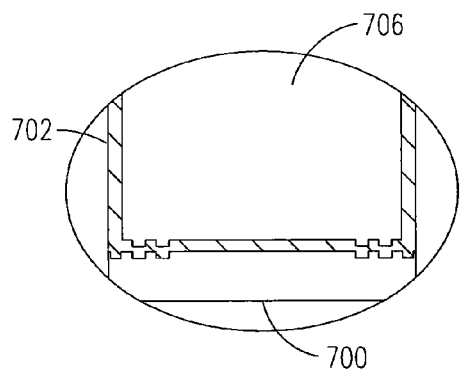
FIG. 7A    FIG. 7B

◉ WELL ONLY WITH BUFFER - FOR REFERENCING
○ WELL WITH COMPOUND

SCREENING SYSTEM AND METHOD FOR ANALYZING A PLURALITY OF BIOSENSORS

CLAIMING BENEFIT OF CO-PENDING APPLICATION

This application is a divisional application of U.S. patent application Ser. No. 11/521,771, filed Sep. 15, 2006, now U.S. Pat. No. 7,976,217.

BACKGROUND OF THE INVENTION

1. Field of the Invention

The present invention relates to a screening system and method for automatically carrying out biochemical, cell biological or molecular biological analyses of liquids at the surfaces of a multiplicity of optical sensors/biosensors which are located in standardized multiwell plates (or other types of multi-vessel systems such as bars, strips, slides, rotor cuvettes etc. . . . ).

2. Description of Related Art

Today there is considerable interest in developing a screening system which can automatically carry out biochemical, cell biological or molecular biological analyses of liquids at the surfaces of a multiplicity of optical sensors/biosensors (or at least on parts of the surfaces of those optical sensors/biosensors) located in standardized multiwell plates (or other multi-vessel systems such as bars, strips, slides, rotor cuvettes etc. . . . ). The targeted analyses often include drug discovery, drug screening, laboratory diagnosis and fundamental research. In these high sensitivity analyses, it is critical that factors which could lead to spurious changes in the measured output (optical response) of the optical sensor/biosensor be carefully controlled or referenced out. The factors which could lead to these spurious changes include, for example, temperature changes, solvent effects, bulk index of refraction changes, and nonspecific binding. The factor which is of interest in this particular discussion is the changing of the temperature.

The use of a standardized multiwell plate in these types of analyses is advantageous because it allows known automated high throughput screening (HTS) systems and known manual fluid handling systems to be used in conjunction with the "special" optical sensors. The most desirable standardized formats are the 96 multiwell plate (9 mm specimen spacing), the 384 multiwell plate (4.5 mm specimen spacing), and the 1536 multiwell plate (2.25 mm specimen spacing). All of these multiwell plates cover the same rectangular area of roughly 130 mm×85 mm. However, the use of the standardized multiwell plate (or any of the other aforementioned multi-vessel systems) can be problematic since it can be difficult to control their temperature profile because their inner wells are not able to adapt as quickly as their outer wells when there is a change in the ambient temperature.

Plus, if the multiwell plate is filled for example with water, then the well contents are going to evaporate at different rates which also makes it difficult to control the temperature profile of the multiwell plate. For example, if the multiwell plate is placed in calm ambient air in an open condition (without a cover), the peripheral regions will evaporate much more quickly than the middle regions, because the air above the wells on the edges is not saturated with water vapor as quickly as the air above the middle wells. As a consequence, these outer wells cool off more quickly due to what is known in this field as evaporation cold. This effect is also present, although quantitatively reduced, if the multiwell plate is provided with a cover.

The liquid handling devices and storages facilities can also adversely affect the temperature profile of the multiwell plate. In particular, when the liquid handling device (pipetting device) is used to transfer liquid onto a target multiwell plate it first takes up liquid from a source vessel (which is open for at least a short time) and then dispenses this liquid onto the target multiwell plate. As a result, the liquid handling device partially transfers to the target plate the temperature profile of the source plate. If the source plate is re-filled by pumps from a supply (bottle, tank, etc.), then considerable temperature profiles may be expected, especially if the source plate is filled through one single inlet opening.

In the past, it has been assumed that the use of incubators to heat the multiwell plates would solve these temperature related problems. Probably, the most widely used automatic incubators are made by Kendro/Liconic and Tomtec which are described in U.S. Pat. Nos. 6,129,428 and 6,478,524 (the contents of which are incorporated by reference herein). In these incubators, the multiwell plates are stored in stacked arrangements such that they are freely accessible from below and can thus be transported into-and-out of the incubators by a shovel-like handler. In addition, the stacked arrangements can be arranged on a support plate which continuously rotates to ensure a better (more homogeneous) temperature of the multiwell plates. Moreover, these incubators can incorporate a blower which is used to provide a not very well-defined intermixing of the air by which the multiwell plates can be further temperature-controlled. Unfortunately, in such incubators, temperature gradients of several degrees is still detectable across the diagonal of a multiwell plate. Also, in these incubators where the temperature control is performed by the air (more generally gas) there is a very slow temperature adjustment with the multiwell plates.

It is known from the literature that this should be able to be done better. For instance, by using a temperature balancing body that contacts the full surface of the bottom of the multiwell plate, the temperature of the multiwell plate can be adjusted in a manner that is faster and more homogeneous (see, DE 3441179 C2 and U.S. Pat. No. 5,459,300 the contents of which are incorporated by reference herein). However, the literature does not describe how the multiwell plates throughput per time unit in a screening system and the temperature balance of those multiwell plates can be suitably realized especially when a screening system is going to be operating at it's sensitivity limit. This problem and other problems are solved by the screening device and method of the present invention.

BRIEF DESCRIPTION OF THE INVENTION

The present invention includes a screening device and a method which can automatically handle and measure (interrogate) a plurality of sensor carriers (i.e., multiwell plates, microplates) with multi-dimensionally arranged, temperature-compensated or temperature-compensatable optical sensors, while maintaining a substantially constant temperature gradient for relatively long period of time around the areas where temperature compensation has been performed on the sensor carriers.

BRIEF DESCRIPTION OF THE DRAWINGS

A more complete understanding of the present invention may be obtained by reference to the following detailed description when taken in conjunction with the accompanying drawings wherein:

FIGS. 6A-6D are various diagrams illustrating an exemplary sensor carrier (microplate) which could be interrogated by the screening system in accordance with the present invention;

FIGS. 7A-7B are diagrams illustrating two different types of sensor carriers (slides) which could be interrogated by the screening system in accordance with the present invention;

DETAILED DESCRIPTION OF THE DRAWINGS

Figure 5A:
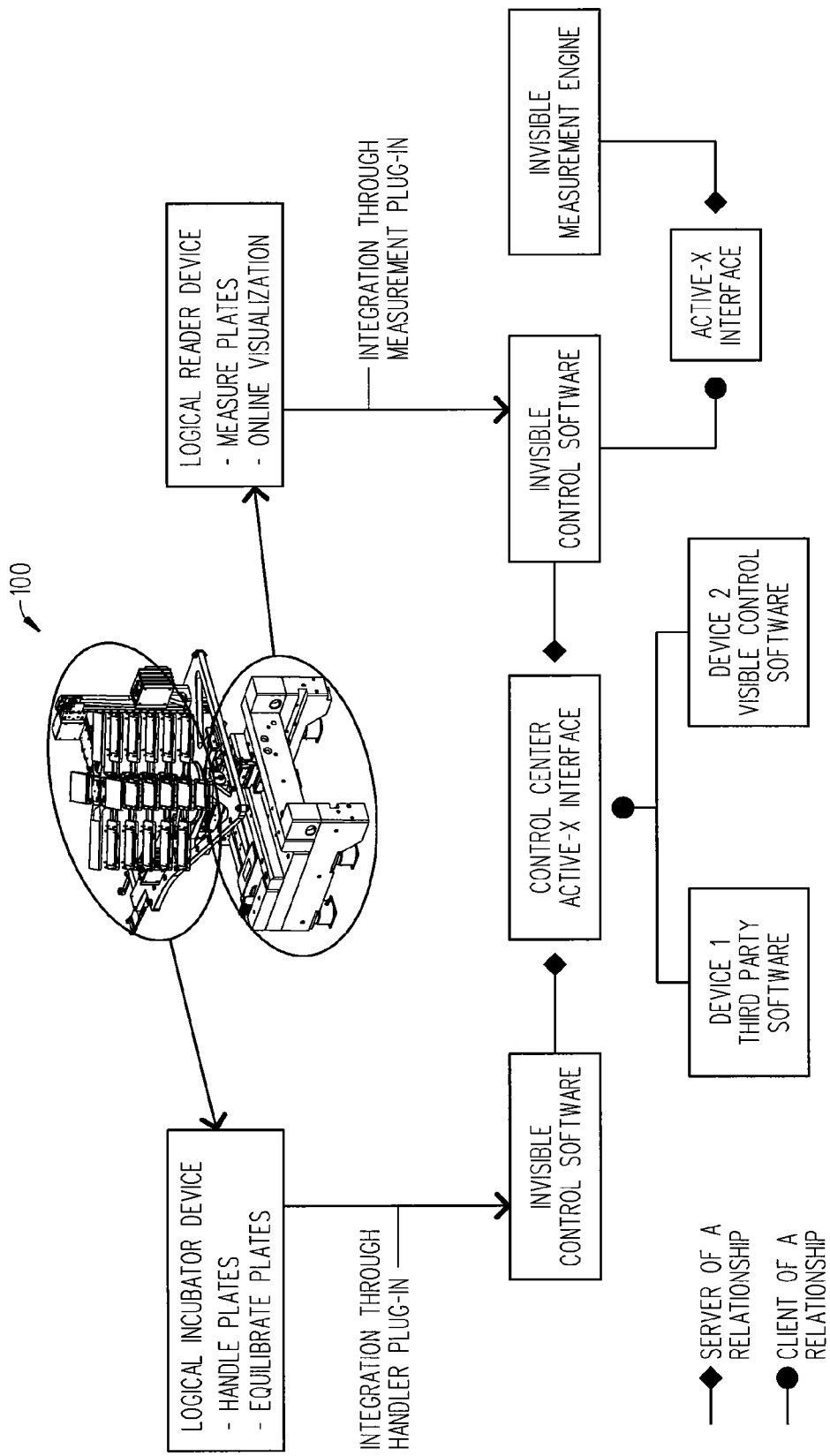
FIGS. 5A-5B are two diagrams which are used to help explain how the screening system can operate in a HTS (parallel) mode in accordance with the present invention.
Figure 5B:
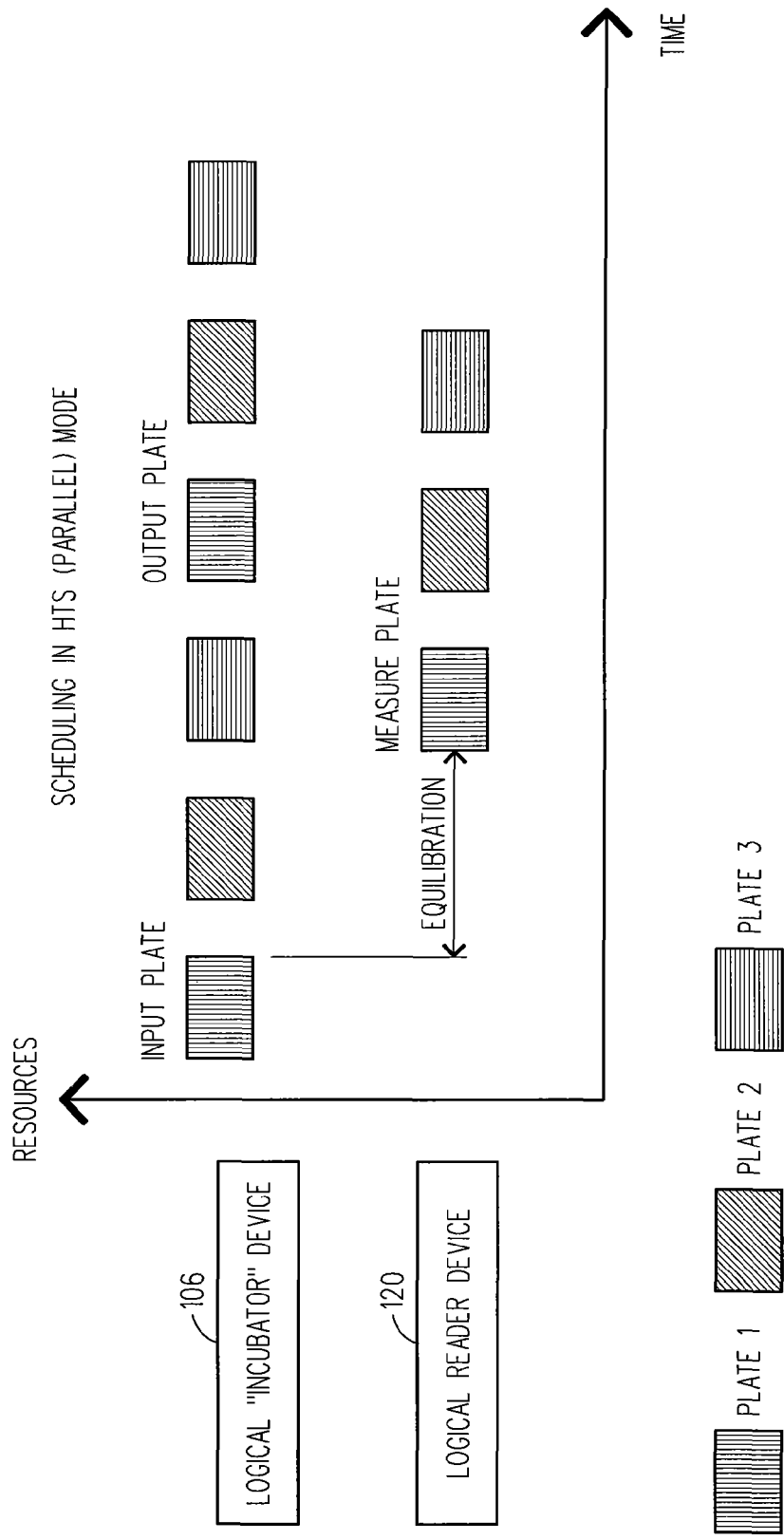
Figure 5C:
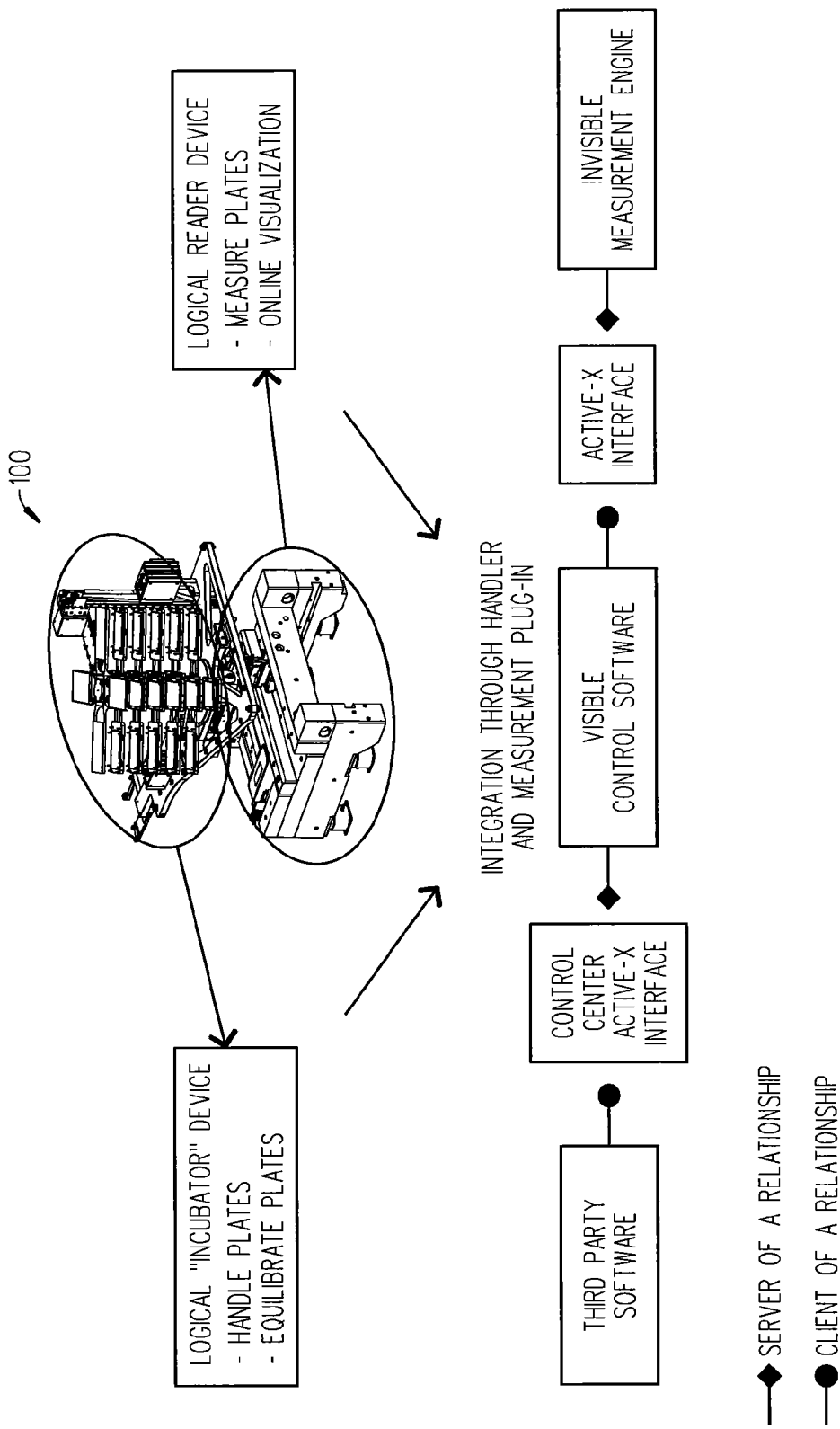
FIGS. 5C-5D are two diagrams which are used to help explain how the screening system can operate in a batch (serial) mode in accordance with the present invention.
Figure 5D:
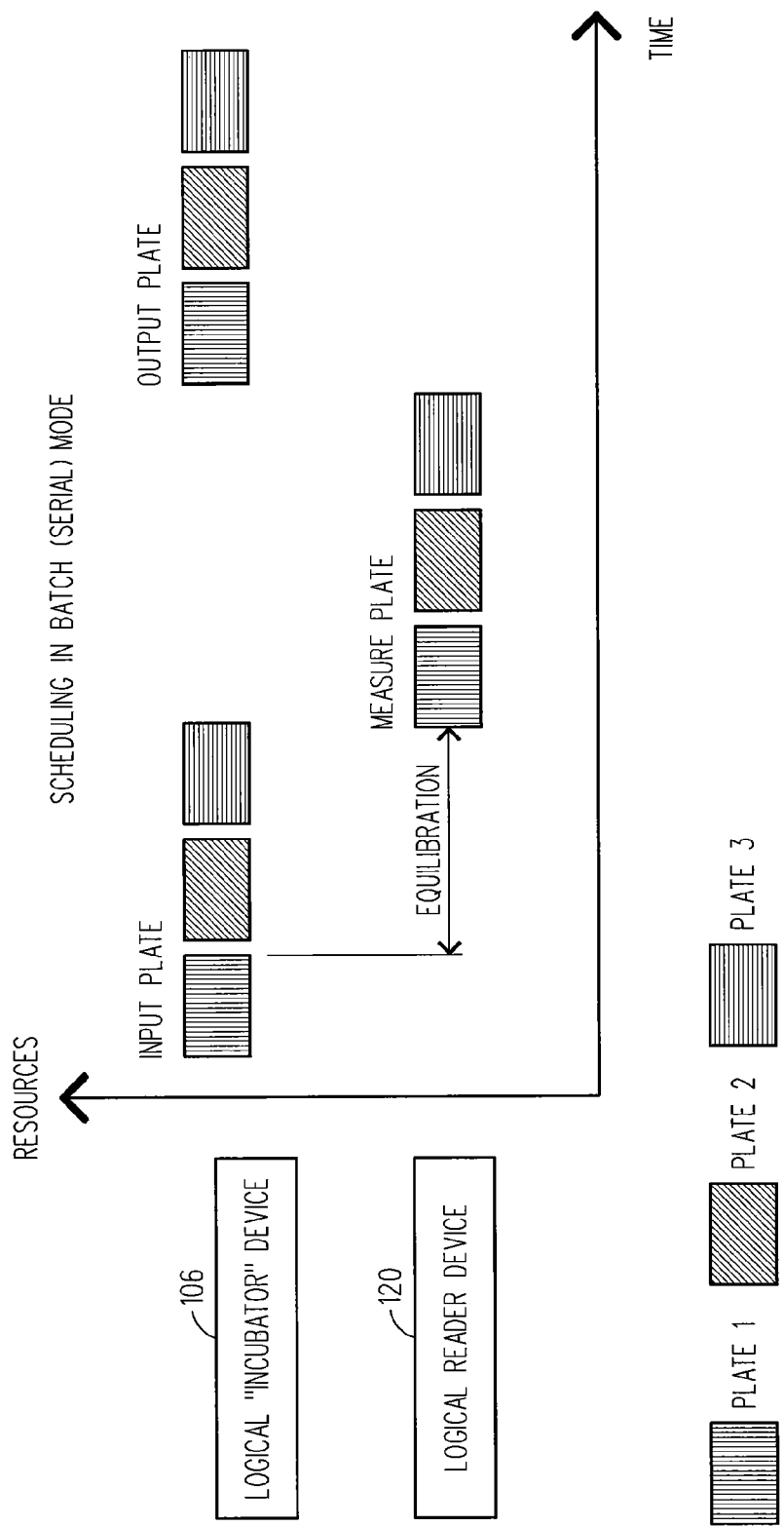
Figure 6A:
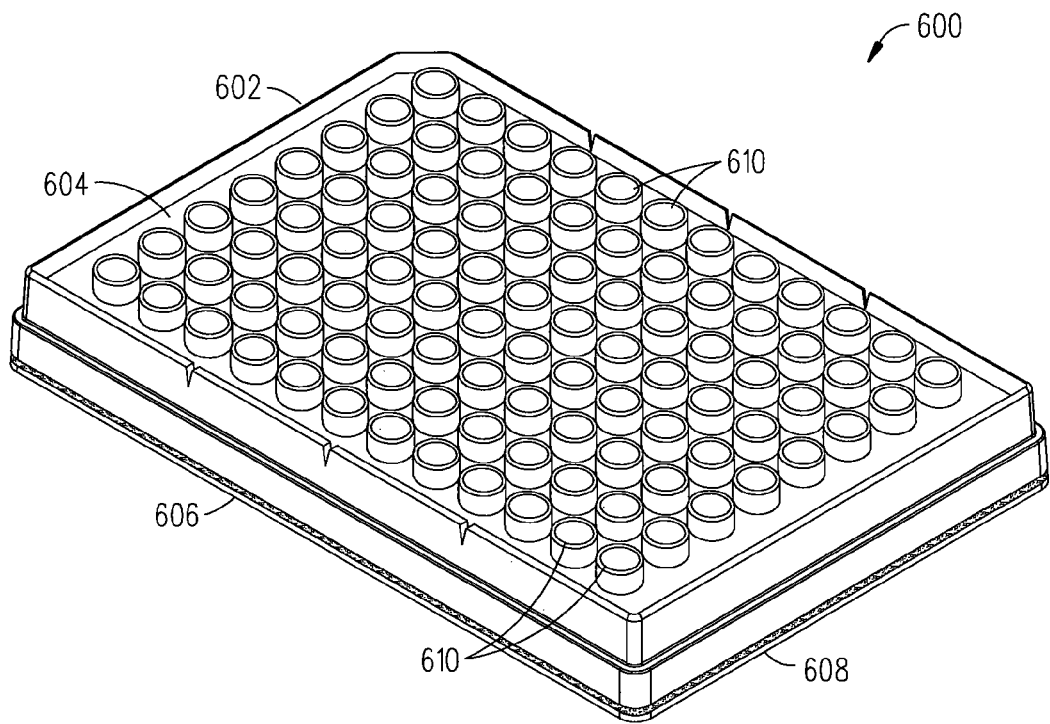
Figure 6B:
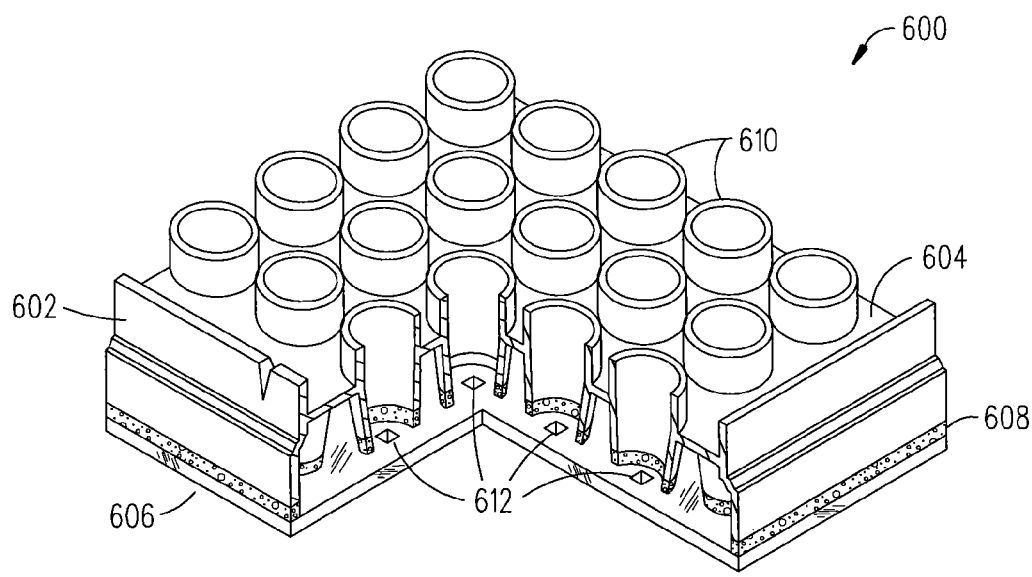

Referring to FIGS. 1-19, there are various diagrams which illustrate a screening system 100 and the various components incorporated therein in accordance with the present invention. As shown in FIGS. 1A-1F, the screening system 100 includes a control unit 102 and a temperature-controlled measurement chamber 104 which contains an equilibration system 106, a measurement system 108 and a handling system 112. Basically, the screening system 100 is designed to automatically handle and measure (interrogate) a plurality of sensor carriers 110 (i.e., multiwell plates 110, microplates 110) with multi-dimensionally arranged, temperature-compensated or temperature-compensatable optical sensors, while maintaining a substantially constant temperature gradient for a relatively long period of time around the areas where temperature compensation has occurred on the sensor carriers 110 (an exemplary microplate 110 is shown in FIGS. 6A-6B).

The screening system 100 is able to perform this measurement (interrogation) by using the equilibration system 106, the measurement system 108 and the special handling system 112. Plus, it may be beneficial if the screening system 100 also included an inside temperature sensor 114 (which measures the temperature of the air/gas within the measurement chamber 104) and an outside temperature sensor 116 (which measures the outside temperature in the vicinity of the screening device 100). Then, the screening systems 100 and in particular the control unit 102 could use the readings from the two sensors 114 and 116 to check whether the measurement chamber 104 is operating in the desired ambient temperature range, which may be important to know so as to meet the necessary prerequisites for a temperature control algorithm.

As shown, the screening device 100 also has a take in/out mechanism 118 (which is mounted to a motor-displaceable frame) for taking a sensor carrier 110 in-and-out of the measurement chamber 104. The take in/out mechanism 118 can cooperate with an outside door of the measurement chamber 104 like a spring forced flap and internally seal the opening against a lock shaft by simple shield, when the outside door is open. This simple lock principle keeps the exchange of air between the measurement chamber 104 and the outside environment to a minimum during the replacement of a sensor carrier 110.

The measurement of the sensor carriers 110 is enabled by positioning one of the sensor carriers 110 relative to a measurement channel or measurement channels associated with a measurement device 120 (part of the measurement system 108) by using a motor-driven x-y moveable table 122 (see FIGS. 2 and 3 for detailed illustrations of an exemplary measurement device 120 and an exemplary x-y moveable table 122)(note: a stationary table may also be utilized). For this purpose, the x-y moveable table 122 has a measurement nest 302 into which a sensor carrier 110 is inserted and then moved so it is positioned in a correct spot over the measurement device 120. In this way, the sensors within the sensor carrier 110 can be sensed or scanned in a definable sequence. For a detailed discussion about some of the different types of measurement devices 120 (and sensor carriers 110) that can be used in this particular application, reference is made to the following documents:

- U.S. patent application Ser. No. 11/489,173 entitled "Label-Free High Throughput Biomolecular Screening System and Method".
- U.S. patent application Ser. No. 11/027,547 entitled "Spatially Scanned Optical Reader System and Method for Using Same".
- U.S. patent application Ser. No. 10/977,520 entitled "Single-Fiber Launch/Receive System for Biosensing Applications".
- U.S. patent application Ser. No. 10/856,572 entitled "Optical Interrogation Systems With Reduced Parasitic Reflections and a Method for Filtering Parasitic Reflections".
- U.S. patent application Ser. No. 11/058,155 entitled "Single Mode (SM) Fiber Optical Reader System and Method for Interrogating Resonant Waveguide-Grating Sensor(s)".
- U.S. patent application Ser. No. 10/602,304 entitled "Optical Interrogation System and Method for Using Same".
- U.S. patent application Ser. No. 11/019,439 entitled "Arrayed Sensor Measurement System and Method"
- U.S. Pat. No. 6,785,433 entitled "Waveguide Grid Array and Optical Measurement Arrangement".
- U.S. patent application Ser. No. 11/100,199 entitled "Optical Interrogation System and Method for 2-D Sensor Arrays".
- U.S. Pat. No. 5,738,825 entitled "Optical Biosensor Matrix.
- U.S. Pat. No. 7,629,173 entitled "Optical Reader System and Method for Monitoring and Correcting Lateral and Angular Misalignments of Label Independent Biosensors".

The contents of these documents are incorporated by reference herein.

Figure 4A:
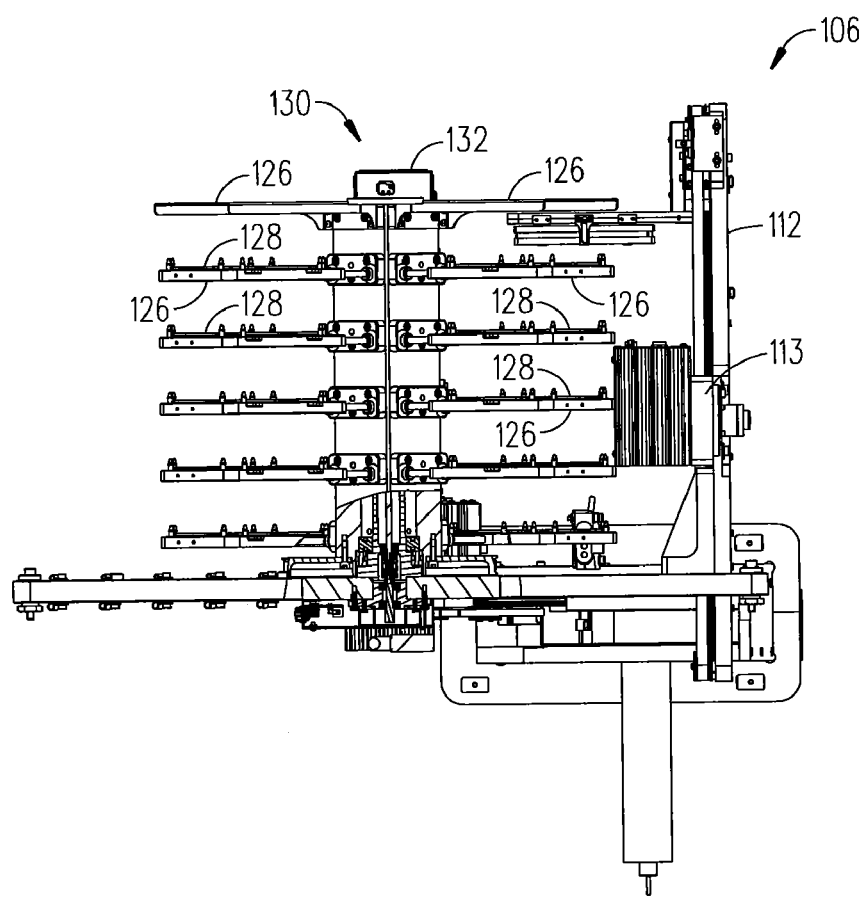
FIGS. 4A-4C are three diagrams illustrating an exemplary equilibration system (with a plurality of temperature compensation bodies) which can be used within the screening system in accordance with the present invention.
Figure 4B:
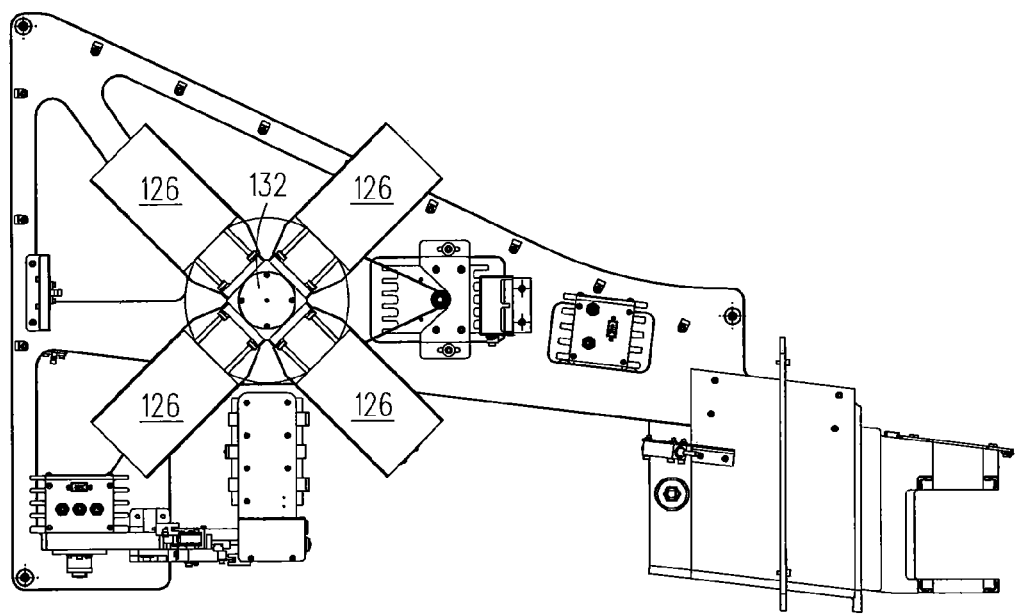
Figure 4C:
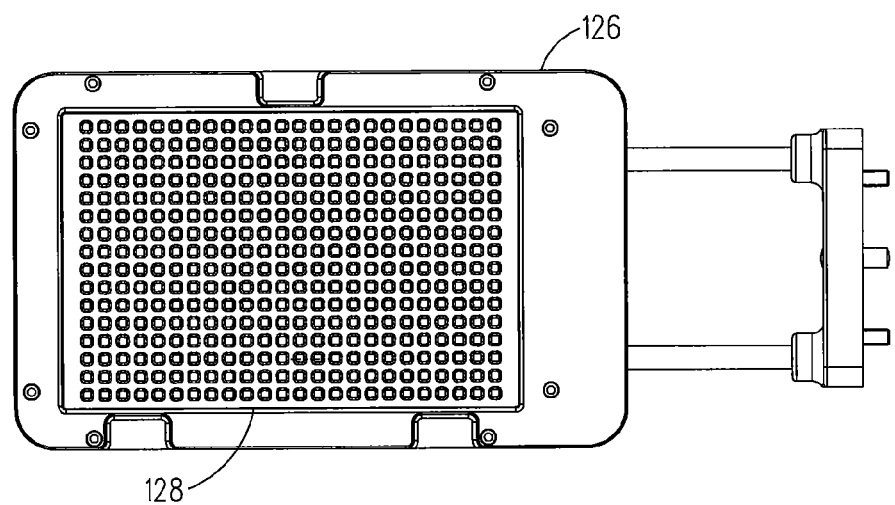

In the measurement chamber 104, there is the special transporting unit 112 (internal plate handling system 112 with a gripper 113) which accepts a sensor carrier 110 from the take in/out mechanism 118 and then deposits the sensor carrier 110 onto a temperature compensation body 128 which is on an equilibration site 126 in the equilibration system 106 (see FIGS. 4A-4C for detailed illustrations of an exemplary equilibration system 106 and an exemplary temperature compensation body 128). After a suitably selected equilibration time, the transporting unit 112 takes the sensor carrier 110 from the temperature compensation body 128 and places it on the x-y moveable table 122 which is moved so the measurement device 120 can interrogate the sensors within the sensor carrier 110. Upon completion of the measurement, the transporting device 112 transfers the sensor carrier 110 to the take in/out mechanism 118 or it takes a detour via the equilibration system 106 from which the sensor carrier 110 is then transferred to the take in/out mechanism 118 and discharged from the screening device 100.

The transporting device 112 can be an automatic manipulator (robot and/or gripper), which receives and transports the sensor carrier 110 in a force- or form-locking manner. The equilibration system 106 has a plurality of temperature compensation bodies 128 which are specifically designed to hold the sensor carriers 110 (see FIGS. 4A-4C and 12-13). Preferably, the specially designed temperature compensation bodies 128 are of such construction that they represent a negative image of the sensor carrier's contour at least in its foot print and, thus, if possible, has full surface contact or at least a maximum possible contact, in terms of the surface, with the sensor carriers 110 (see FIG. 4C which shows temperature compensation body 128 for a 384-well RWG sensor carrier 110). Moreover, the specially designed temperature compensation bodies 128 have a sufficiently great heat capacity (thermal conductance) such that when the sensor carriers 110 are placed on them then those bodies 128 will not experience a substantial change in temperature. This can be satisfied if it is assumed that an initial temperature of the sensor carriers 110 does not differ too much from a defined temperature (i.e., approximately 3 to 5° C.) within the measurement chamber 104.

Moreover, the specially designed temperature compensation bodies 128 could have a relatively low surface resistance with the sensor carriers 110 such that any difference in heat can be quickly compensated. A suitable surface resistance should be achieved if there is a maximum identity and a low depth of roughness between the surfaces of the temperature compensation bodies 128 and the sensor carriers 110. The surface resistance could also be reduced by pressing or sucking the sensor carriers 110 against the temperature compensation bodies 128. Furthermore, the surface resistance could be reduced by increasing the mass of the sensor carriers 110. For instance, the mass of the sensor carriers 110 themselves can be increased by placing covers/foils or a special heavy lid on top of them (the covers/foils also helps prevent the evaporation of the liquids from the sensor carriers 110). If desired, the covers can be constructed specifically to be adapted to the particular geometry of the sensor carriers 110. Or, the covers can be produced such that they are disposable. Alternatively, the covers can have a thin metal plate mounted/placed thereon to add the desired additional mass to the sensor carriers 110. Of course, it is important that the above-mentioned handling system 112, e.g. the gripper 113, can transport these covers.

The storage of the sensor carriers 110 can be effected within the equilibration system 106 according to a simple FIFO (first in first out) scheme. This could be accomplished in several ways, for example, the equilibration system 106 could allow random access to the equilibration sites 126 and then use the control unit 102 to implement the FIFO scheme. Or, the equilibration system 106 itself can be constructed as a mechanical FIFO storage system. In contrast, it is also possible to have an equilibration system 106 that utilizes a LIFO (last in first out) storage scheme by following a restacking algorithm which would be implemented by the control unit 102. Of course, the LIFO scheme could be difficult to successfully perform because it requires the plate carousel 130 to constantly move within the equilibration system 106.

The storage capacity, i.e. the number of equilibration sites at which the sensor carriers 110 can contact the temperature compensation bodies 128, depends on the equilibrating time which is required to achieve a sufficiently good, homogeneous heat distribution on the sensor carriers 110. An important factor to consider in this connection is how great a temperature difference between the sample site and the reference site is allowed and how great the distance is between these two sites. If, for example, a 384-well microplate 110 is used, and only every other well is filled with compounds to examine binding, then referencing can be effected in each case with the next well that is filled only with a buffer, the distance between both sites is thus 4.5 mm. Such a great distance would typically require that the 384-well microplate 110 spend a correspondingly prolonged equilibration time on the temperature compensation body 128.

In contrast, if referencing is effected within the well, then the distance between sites can be reduced to approximately 1 mm, thus reducing the required equilibration time that the 384-well microplate 110 needs to spend on the temperature compensation body 128. The last scenario would result in fewer temperature compensation bodies 128 being needed in the equilibration system 106. Lastly, it should be appreciated that the storage capacity is also related to the desired quality of measurement (coefficient of variation), the resolution of the method of measurement (molecule size ratio of the binding partners) and the accepted average temperature of the incoming sensor carriers 110.

Preferably, the measurement device 120 (and x-y moveable table 122) is located at a minimum possible distance from the equilibration system 106 and the handling system 112. Both the measurement device 120 and the handling system 112 should be constructed such that they each have a short and spot contact with the sensor carrier 110. This helps prevent a change in the temperature distribution, set by the equilibration system 106, from being made on the sensor carrier 110. Moreover, it should be ensured that the handling system 112 transports the sensor carrier 110 sufficiently quickly so as to prevent any noticeable change in the temperature profile of the sensor carrier 110. Any interruption of this transport and the subsequent measurement of the sensor carrier 100 should not be permitted by the control unit 102.

If desired, the screening system 100 can include one or more temperature sensors 118a which are positioned near the opening of the take in/out mechanism 118. The temperature sensor(s) allow the control unit 102 to determine the temperature of an incoming sensor carrier 110 in a non-contacting manner and to check whether the intended storage time of that sensor carrier 110 is sufficient for temperature equilibration purposes. Alternatively, the control unit 102 can use this type of temperature reading to calculate the time that the incoming sensor carrier 110 needs to be placed on the temperature compensation body 128 to obtain the desired temperature profile on the sensor carrier 110. Of course, a wide variety of temperature sensor(s) can be used to perform this measurement such as infrared sensors, electronic contact thermometers, or a combination of color sensors and temperature-sensitive dyes (e.g. liquid crystals or fluorescent lanthanoid-ligand complexes) which are placed on the incoming sensor carrier 110. Plus, it is to be expected that radio-frequency based transponders are going to replace the identification barcode labels which are commonly used today to identify sensor carriers 110 (microplates 110). As an additional function, these electronic radio-frequency based transponders could transmit the current temperature of the sensor carrier 110, if their semi-conductor structure also has a temperature-sensitive range of operation.

These temperature sensor(s) may also provide important information in connection with an optional calculation of the dew point. For this purpose, the temperature of the incoming sensor carrier 110, the temperature inside the measurement chamber 104 and the air humidity inside the measurement chamber 104 are used to calculate whether there is a risk of water condensing on the sensor carrier 110. There would be a risk of water condensing on the sensor carrier 110 if the sensor carrier 110 is colder than the air inside the measurement chamber 104. Since, part of the sensor carrier 110 is going to be in direct mechanical contact with a temperature compensation body 128, this condensate could possibly affect the temperature equilibration. Plus, this condensation could also interfere with the optical sensor light path used by the measurement device 120 to interrogate the sensors in the sensor carrier 110. Excessive pollution of the temperature compensation bodies 128 would be a further undesired consequence of water condensation in the long run. The information concerning the air humidity may be obtained by using an electronic sensor (e.g., SENSIRION, Switzerland) which would be placed in the measurement chamber 104. Or, the air humidity may be obtained by using an external source of information, e.g. a LIMS (Laboratory Information Management System).

If the control unit 102 determines that the incoming sensor carrier 110 has an admissible temperature, then the sensor carrier 110 is transported to and deposited onto one of the temperature compensation bodies 128. In contrast, if the incoming sensor carrier 110 does not have an admissible temperature, then the control unit 102 makes a case-based differentiation. For instance, if the sensor carrier 110 has an inadmissible temperature and there is little risk of water condensing, then the control unit 102 can instruct that the sensor carrier 110 be transported to and deposited onto one of the temperature compensation bodies 128. However, the control unit 102 should at least make an entry into a data file associated with this particular sensor carrier 110 which indicates that the incoming temperature was inadmissible. Or, the control unit 102 can simply reject the sensor carrier 110 if it does not have an admissible temperature.

The implementation of this particular procedure can have far-reaching and important consequences. For instance, this procedure can place considerable work on the control unit 102 and in particular on the automatization software, work flow manager and/or scheduler. Thus, it is desirable if the sensor carriers 110 are temporarily stored in an external plate storage system, i.e. incubated in advance at room temperature, for a predetermined amount of time before they are placed within the screening system 100. This is not necessarily a disadvantage since the binding of molecules to the surface of the sensors often requires a certain amount of incubation time and thus, during automatic operation, this pre-incubation already needs to be performed. If the screening system 100 is controlled by suitable software (for example, a scheduler), then these incubation times would have little effect (during the start-up phase of a screen) on the throughput of the sensor carriers 110. Such external incubators or storage units are often referred to as microplate hotels and are manufactured by, for example, Liconic or Kendro/Thermo.

A description is provided next about three exemplary ways the screening system 100 could be used to perform measurement assays (e.g., stand alone assays, scheduler controlled assays). To help describe some of the different ways that the screening system 100 could be used it is useful to recall that the screening system 100 includes the following components: the take in/out mechanism 118 (plate carriage 118), the handling system 112 (plate gripper 113), the equilibration system 106 (including a rotating plate carousel 130 with multiple levels and quadrants of temperature compensation bodies 128), the measurement system 120 (including the measuring module 108) (see FIGS. 1A-1F). Plus, the screening system 100 has an entry/exit door (flap) that is closed by a spring force when the take in/out mechanism 118 is not in an outside position. The preferred plate handler 112 can be a vertical mobile system which can reach all levels of the plate carousel 130 (in particular it can reach between the individual temperature compensation bodies 128 on anyone carousel level), the take in/out mechanism 118 and the measurement nest 302 on the x-y moveable table 122. In this example, the plate carousel 130 has several levels (shown five levels) each of which are divided up into four quadrants on which there are secured the specially designed temperature compensation bodies 128 (see FIGS. 4A-4C and 12-13).

In the first example, the screening system 100 can be used to perform a stand alone measurement assay by:

1. Putting a sensor carrier 110 onto the take in/out mechanism 118 (via hand or robot).

2. Moving the take in/out mechanism 118 into the measurement chamber 104 via a door and positioning the sensor carrier 110 below a gripper 113 on the handling system 112.

3. Grabbing the sensor carrier 110 using the gripper 113 on the handling system 112.

4. Placing the sensor carrier 110 into the measurement nest 302 of the x-y moveable table 122 located above the measurement system 108.

5. Interrogating the sensor carrier 110.

6. Taking the sensor carrier 110 from the x-y moveable table 122 and moving it to the take in/out mechanism 118.

7. Moving the sensor carrier 110 out of the measurement chamber 104 via the door.

In the second example, the screening system 100 can be used to perform a scheduled controlled measurement assay by:

1. Putting a sensor carrier 110 onto the take in/out mechanism 118 (via hand or robot).

2. Moving the take in/out mechanism 118 into the measurement chamber 104 via a door and positioning the sensor carrier 110 below a gripper 113 on the handling system 112.

3. Grabbing the sensor carrier 110 using the gripper 113 on the handling system 112.

4. Moving the sensor carrier 110 to a desired level between two quadrants on the plate carousel 130.

5. Turning the plate carousel 130 to the target position.

6. Placing the sensor carrier 110 onto the desired temperature compensation body 128 located on the plate carousel 130 (start the temperature equilibration).

7. Moving the temperature equilibrated sensor carrier 110 from the plate'carousel 130 with the gripper 113 on the handling system 112 (if desired one can move another temperature equilibrated sensor carrier 110).

8. Placing the sensor carrier 110 into the measurement nest 302 of the x-y moveable table 122 which is located above the measurement system 108.

9. Interrogating the sensor carrier 110.

10. Taking the sensor carrier 110 from the x-y moveable table 122 and moving it to the take in/out mechanism 118.

11. Moving the sensor carrier 110 out of the measurement chamber 104 via the door.

In the third example, the screening system 100 can be used to perform a scheduled controlled measurement assay by:

1. Putting a sensor carrier 110 onto the take in/out mechanism 118 (via hand or robot).

2. Moving the take in/out mechanism 118 into the measurement chamber 104 via a door and positioning the sensor carrier 110 below a gripper 113 on the handling system 112.

3. Grabbing the sensor carrier 110 using the gripper 113 on the handling system 112.

4. Moving the sensor carrier 110 to a desired level between two quadrants on the plate carousel 130.

5. Turning the plate carousel 130 to the target position.

6. Placing the sensor carrier 110 onto the desired temperature compensation body 128 located on the plate carousel 130 (start the temperature equilibration).

7. Moving the temperature equilibrated sensor carrier 110 from the plate carousel 130 with the gripper 113 on the handling system 112 (if desired one can move another temperature equilibrated sensor carrier 110).

8. Placing the sensor carrier 110 into the measurement nest 302 of the x-y moveable table 122 which is located above the measurement system 108.

9. Interrogating the sensor carrier 110.

10. Taking the sensor carrier 110 from the x-y moveable table and moving it to a free temperature compensation body 128 on the plate carousel 130 only for parking/holding to have more freedom for the scheduling software.

11. Taking the sensor carrier 110 from the plate carousel 130 and moving it to the take in/out mechanism 118.

12. Moving the sensor carrier 110 out of the measurement chamber 104 via the door.

Of course, these three exemplary ways are not the only ways one can perform a measurement assay using the screening system 100. For instance, the screening system 100 can be operated in a HTS (parallel) mode in which a large number of sensor carriers 110 are placed in the measurement chamber 104 and one-by-one the sensor carriers 110 are interrogated by the measurement system 108. FIGS. 5A-5B illustrate an exemplary software design which could be used when the screening system 100 is operating in the HTS (parallel) mode. Alternatively, the screening system 100 can be operated in a batch (serial) mode in which a large number of sensor carriers 110 are placed in the measurement chamber 104 and one-by-one the sensor carriers interrogated by the measurement system 108. FIGS. 5C-5D illustrate an exemplary software design which could be used when the screening system 100 is operating in the batch (serial) mode.

A description is provided next about different aspects and possible alternatives associated with the screening system 100 that can be used or implemented when performing a measurement assay in accordance with the present invention. The topics discussed below are as follows:

1. Sensor carrier as microplate.
2. Sensor carrier as slide.
3. Sensor carrier as cuvette rotor with flow through cuvette sensor.
4. Temperature distribution in microplates.
   4.1 Temperature compensation interrogation scheme with adjacent well.
   4.2 Temperature compensation interrogation scheme within a well.
5. Temperature compensation body for RIFS transducer/sensor.
6. Temperature compensation body for grating coupler.
7. Temperature compensation body for SPR sensor.
8. Temperature compensation body for waveguide interferometer.
9. Automatic measurement chamber.
10. Measuring device for grating sensors.
11. Equilibration operation in a microplate.
12. Measuring device for waveguide interferometers.
13. Measuring device for RIFS transducers/sensors.

1. Sensor Carrier 110 as a Microplate:

A typical microplate 600 arrangement according to the SBS standard (Journal of Biomolecular Screening, Vol 1, Number 4, 1996, pp. 163-168) consists of a frame 602, including a well structure 604 (holey plate 604) that can be made of a plastic material, in most cases polystyrene, polypropylene or Cyclic Olefin Co-Polymer (f.e. Topas™), and of a bottom 606 that can be made of glass (see FIGS. 6A and 6B for drawings of an exemplary 96-well microplate 600). The well structure 604 can be attached to the bottom 606 via adhesives 608, injection molding, ultrasonic bonding, laser or infrared welding etc. . . . .

In preparation for binding experiments, the target molecules can be placed at the bottoms of the wells 610 in the microplate 600 by using a conventional liquid handling system (not shown). A biosensor 612 is shown located at the bottom of each well 610. In one embodiment, FIG. 6C shows a side-view of a resonant waveguide grating (RWG) biosensor 612 (which has an optical grating structure 614) that is located in a well 610 as discussed in U.S. Pat. No. 4,815,843 (the contents of which are incorporated by reference herein). Alternatively, FIG. 6D shows a side-view of another type of biosensor 612 known as a Reflectometric Interference Spectroscopy (RIFS) sensor 612 that is discussed in U.S. Pat. No. 6,018,388 (the contents of which are incorporated by reference herein).

2. Sensor Carrier 110 as a Slide:

Another important format which has been used in laboratories for considerably more years than microplates is the microscope specimen carrier, commonly referred to as a slide (see FIGS. 7A-7B which illustrate an exemplary slide 700). The typical slide 700 has a size of 25×75 mm$^2$ and is made from a planar glass plate or plastic plate. The basic dimensions of such slides 700 have been standardized by microscope manufacturers. The slide 700 shown also has wells 702 fitted thereon or attached thereto. These wells 702 are rubber-sealed against or connected to the planar plate by the methods already mentioned above with regard to the microplate 600. Wells 702 made of silicone rubber which are attached to glass are also known, and so are wall-free, planar glass structures with alternating hydrophobic (better: ultraphobic) and hydrophilic (better: ultraphilic) regions. On these slides 700, the optical structures/biosensors 612 already mentioned above can be mounted/formed.

Alternatively, these slides 700 can have formed thereon micro-optical interferometers 706 in which light can be coupled in-and-out via planar grating couplers (see FIG. 7B for a side view of an exemplary micro-optical interferometer 706 which could be used in microplate 600). If such structures (wells 702 with biosensors 704 or micro-optical interferometers 706) are realized within a 9 mm grid, then these slides 700 would be compatible with the double 8-well strips of conventional microplates. As such, these slides 700 can be placed on carrier frames which have microplate foot prints so they can be handled within the screening system 100.

3. Cuvette Rotors

Figure 8A:
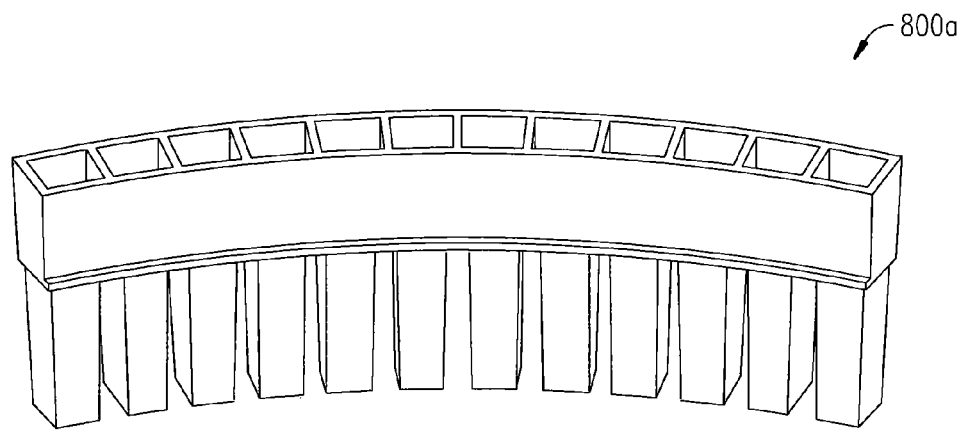
FIGS. 8A-8B are diagrams illustrating two different types of sensor carriers (cuvette systems) which could be interrogated by the screening system in accordance with the present invention.
Figure 8B:
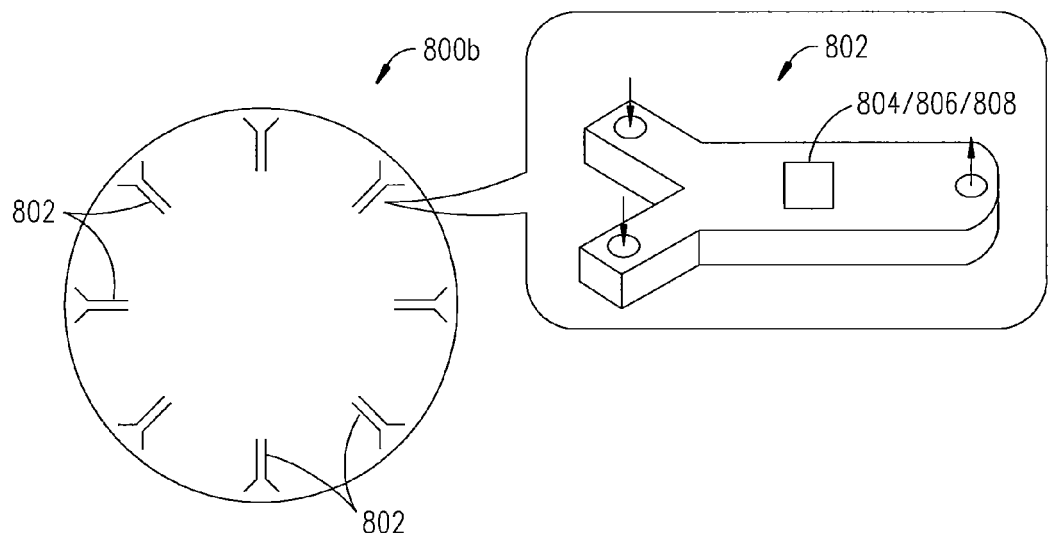

In the diagnostic industry, a wide-range of cuvette systems have been used including cuvette strips/bars 800a and rotor cuvette systems 800b (see FIGS. 8A-8B). For example, the rotor cuvette system 800b is often employed in combination with a 1-channel liquid handling arrangement and since it can be mounted directly on a rotary axis it can be very easy to position with respect to devices for liquid handling or measurement. The typical rotor cuvette system 800b is an injection molded article which is made from the same plastic materials as those commonly used to make microplates. The exemplary rotor cuvette system 800b shown has 8 individual Y-flow through cuvettes 802 where each cuvette 802 can contain a grating biosensor 804, an optical transducer structure 806, or micro-optical interferometers 808 (for example). This rotor cuvette system 800b can also be optimized for measurements of absorbence, fluorescence or luminescence, and some of the best known manufacturers of these devices are Hitachi and Olympus. The screening system 100 and the various principles of measurement described herein can be utilized to interrogate such cuvette structures 800a and 800b.

4. Temperature Distribution in Microplates

Figure 9A:
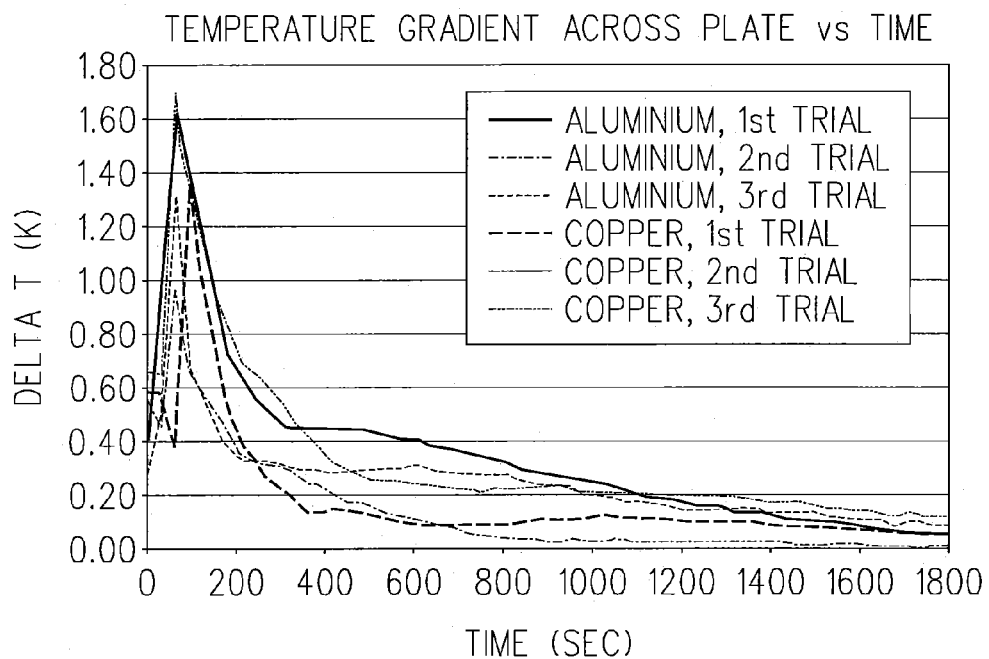
FIGS. 9A-9C are diagrams illustrating the temperature distribution associated with two exemplary microplates which are used to help indicate an advantage of using the screening system in accordance with the present invention.
Figure 9B:
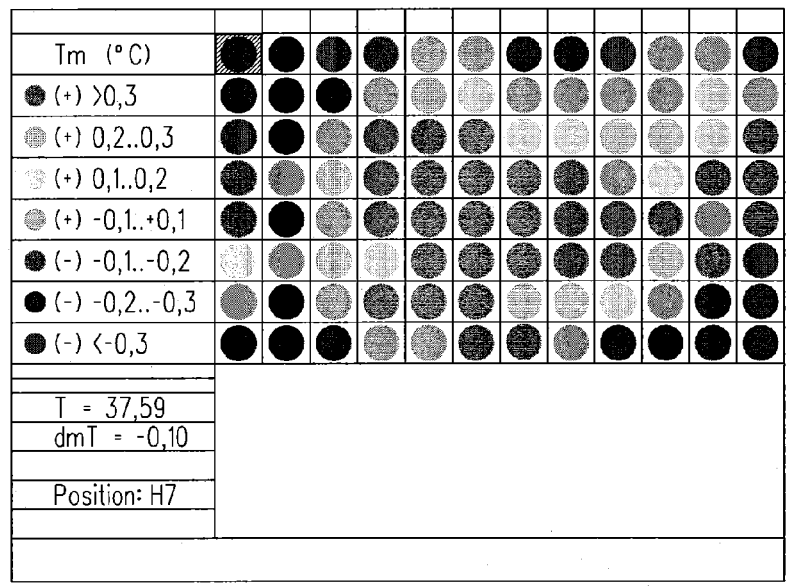
Figure 9C:
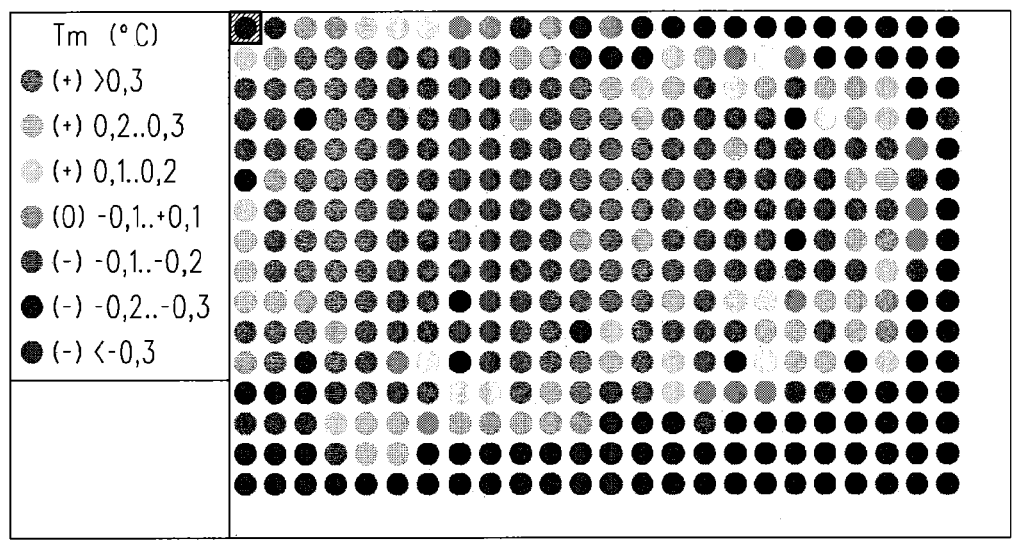
Figure 10:
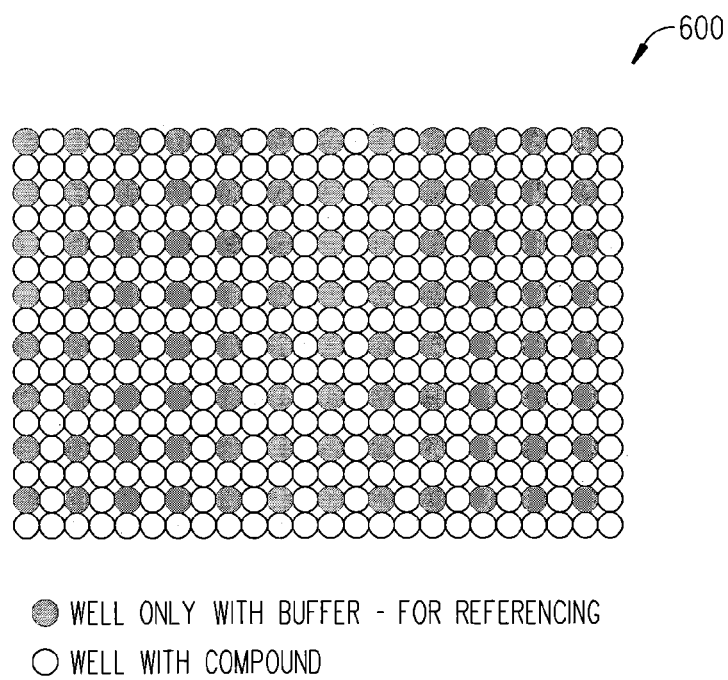
FIG. 10 is a diagram which is used to help explain how the screening system can compensate for temperature changes by interrogating both sample wells and reference wells within a microplate in accordance with the present invention.

A discussion about the temperature distribution of two different microplates 600 which where placed in temperature compensation bodies 128 is provided next with reference to FIGS. 9A-9C. The data shown in FIG. 9A was obtained using miniature thermocouplers made of 50 µm thick alumel and chromel wires. These thermocouplers had a low heat capacity and high temperature resolution thus they where very well suited for temperature measurement tasks in microplate wells. FIG. 9A shows the speed of thermal equilibration. In contrast, the temperature measurement shown in FIG. 9B was effected with a cresol red dye mixture in a 96-well microplate 600 that was interrogated by a commercially available microplate reader operating at a transmission of 405 nm. While, FIG. 9C illustrate the readings associated with a 384-well microplate 600 containing a temperature-sensitive fluorescence indicator which was interrogated by a commercially available microplate fluorescence reader. As can be seen, the temperature compensation bodies 128 helped address problematical fluctuations in temperatures within these microplates 600. Other ways that can be used to help compensate for temperature fluctuations in addition to the equilibration system 106 are discussed next:

4.1 Temperature Compensation Interrogation Scheme with the Adjacent Well in a Microplate One method which can also help compensate for temperature fluctuating during measurements of binding events in microplates 600 involves the alternating use, with respect to columns or lines, of sample wells and reference (buffer) wells within the microplate 600. This is achieved, for example, by using a 96 pipettor having an indexing mechanism to apply 288 well sample array and 96 well buffer array to a 384-well microplate according to the diagram shown in FIG. 10.

4.2 Temperature Compensation Interrogation Scheme within a Single Well in a Microplate Another method which can also help compensate for temperature fluctuations involves the interrogation of a single well which has both a reference region and a sample region. In this interrogation scheme, each well has a biosensor therein with a diffraction grating structure that has a blocked region which does not interact with a sample and is thus suitable to be used as a reference area for comparison with the rest of the diffraction grating that has the sample located thereon (see FIG. 11A). The close proximity of the reference region to the sample region helps to considerably improve the compensation of the temperature especially when compared to the method which uses adjacent wells. Plus, this particular interrogation scheme utilizes less wells when compared to the method which uses adjacent reference and sample wells to take into account temperature fluctuations.

Figure 11A:
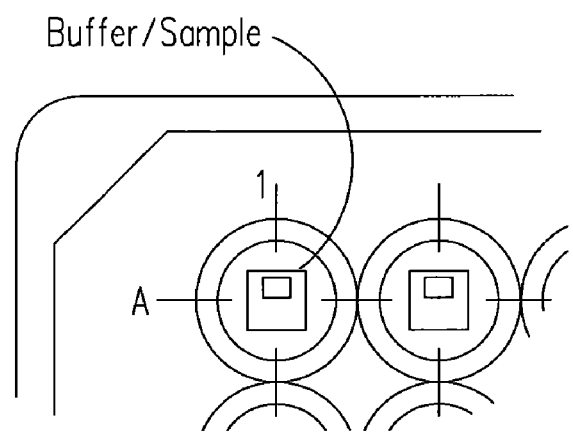
FIGS. 11A-11B are diagrams which are used to help explain how the screening system can compensate for temperature changes by interrogating both sample regions and buffer regions within single wells of a microplate in accordance with the present invention.
Figure 11B:
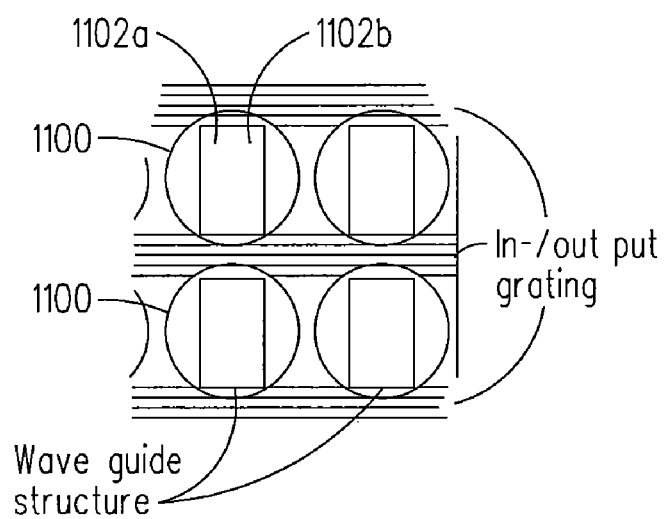

Alternatively, interferometric sensors 1100 which have at least two measuring arms 1102a and 1102 can be used in this particular interrogation scheme (see FIG. 11B). In this case, a comparable temperature compensation effect can be obtained, because the signal of the interferometer is actually generated, as a matter of principle, during superposition of two optical paths. Thus, if both paths are located under the influence of the liquid of one well, then the temperature difference between the two paths decreases with the increasing geometrical proximity of the two paths. FIG. 11B illustrates exemplary interferometric sensors 1100 which have two measuring arms 1102a and 1102b.

5.0 Temperature Compensation Body for RIFS Transducer/Sensor

Figure 12:
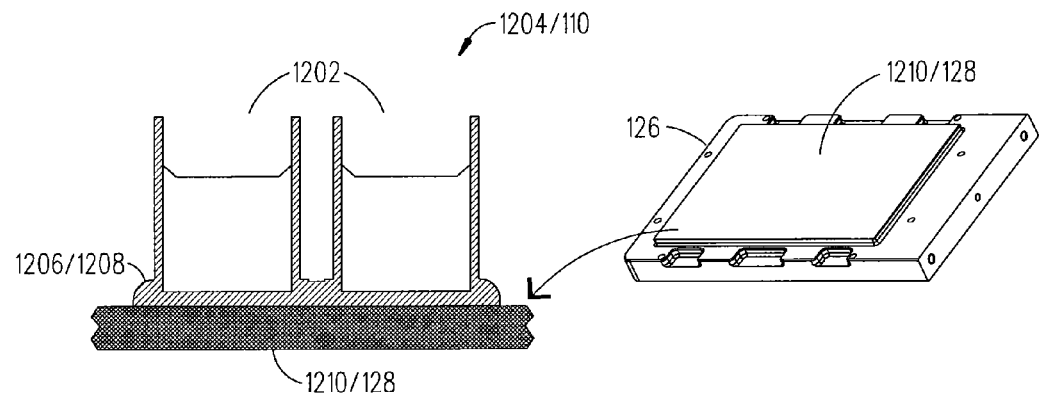
FIG. 12 is a block diagram illustrating an exemplary temperature compensation body (located in the equilibration system of FIGS. 4A-4C) that can be used to help equalize the temperature of a microplate which incorporates RIFS transducers in accordance with the present invention.

FIG. 12 is a block diagram illustrating a couple of wells 1202 in a microplate 1204 (sensor carrier 110) which has a glass bottom plate 1206 that is configured as an RIFS transducer 1208 which is in full surface contact with a flat temperature compensation body 1210 (e.g. flat metal block of copper or aluminum). If the microplate 1204 and in particular the RIFS transducer 1208 is in full contact with the metal block 1210 (that is located on the plate carousel 130) for a sufficiently long time, then the temperature differences between the wells 1202 are going to be compensated.

6.0 Temperature Compensation Body for Grating Sensors

Figure 13:
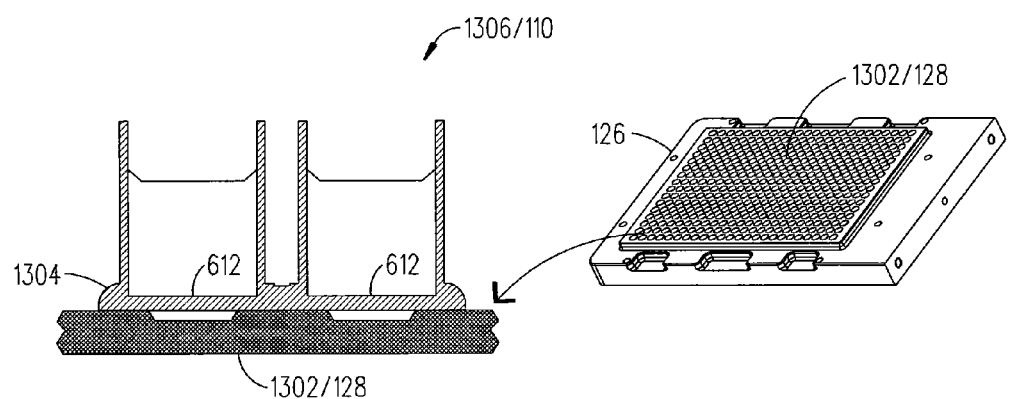
FIG. 13 is a block diagram illustrating an exemplary temperature compensation body (located in the equilibration system of FIGS. 4A-4C) that can be used to help equalize the temperature of a microplate which incorporates RWG biosensors in accordance with the present invention.

FIG. 13 shows an exemplary "pitted" thermal bridge 1302 (temperature compensation body 1302) which can be used for the temperature compensation of the bottom 1304 of a microplate 1306 (sensor carrier 110) (which contains grating sensors 612). Alternatively, the entire bottom 1304 of the microplate 1306 may contact the entire surface of a flat metal block. However, if the microplate 1306 has a glass bottom 1304 then this alternative may not work well since there is a risk of damaging the diffraction grating etc. . . . . . This risk is even more prevalent when the microplate 1306 has a plastic bottom 1304 which means that if there are "pits" in the region of the diffraction grating/sensor then this helps ensure greater safety and at the same time helps ensure a sufficiently quick temperature compensation.

Figures 14, 15:
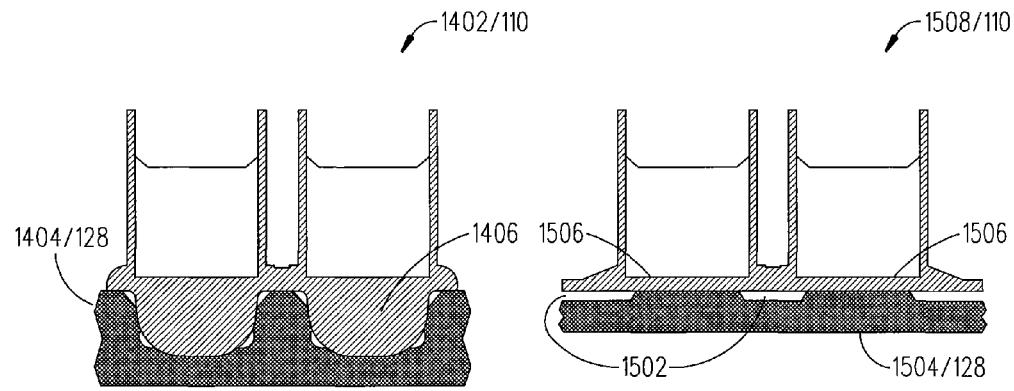
FIG. 14 is a block diagram illustrating an exemplary temperature compensation body (located in the equilibration system of FIGS. 4A-4C) that can be used to help equalize the temperature of a microplate which incorporates SPR biosensors in accordance with the present invention.
FIG. 15 is a block diagram illustrating an exemplary temperature compensation body (located in the equilibration system of FIGS. 4A-4C) that can be used to help equalize the temperature of a microplate which incorporates waveguide interferometers in accordance with the present invention.

7. Temperature Compensation Body for Surface Plasmon Resonance (SPR) Sensors Compared with the two preceding temperature compensation bodies 1210 and 1302 designed to interface with microplates 1204 and 1306 which have planar bottoms, there can be specially designed temperature compensation bodies 128 that provide temperature compensation for microplates with more complex bottoms. For instance, FIG. 14 shows a portion of a SPR microplate 1402 (sensor carrier 110) which is placed on top of a temperature compensation body 1404 whose topology is essentially a negative of the topology of the SPR sensor's bottoms 1406.

8. Temperature Compensation Body for Waveguide Interferometer

As was the case which was described above with the grating sensors, it is also possible to adapt a temperature compensation body 1504 to match the planar bottom of a microplate 1508 (sensor carrier 110) which has waveguide interferometers 1506 located therein. In this case, to reduce the risk of local damage, a pit-shaped recess 1502 is provided in the temperature compensation body 1504 near the region of the coupling-in and coupling-out gratings of the waveguide interferometers 1506. In contrast, to the simple grating sensor, the temperature compensation is effected in this case by having direct contact with the sensor region. This is possible because the sites of the recesses 1502, i.e. the coupling-in and coupling-out regions, have a geometrical distance from the sensor 1506.

If desired, the microplate 1508 (and other sensor carriers 110) may have a bottom coated with a substance to help optimize the surface resistance with a temperature compensation body 1504 (or other temperature compensation bodies 128). For instance, the microplate 1508 (and other sensor carriers 110) can have their bottoms coated with a galvanic coating like the one commonly used to manufacture circuit boards. Although such coatings have only a comparatively low heat capacity, they can still help ensure a very quick temperature distribution and a very good thermal contact with a temperature compensation body 128.

9. Measurement Chamber 104/Handling System 112/Equilibration System 106 (see FIGS. 1A-1B)

In one embodiment, the exemplary measurement chamber 104 is a thermally insulated, temperature-controlled vessel within which a temperature of 3° C. above room temperature is usually maintained. The temperature control can be effected by a circulated air system whose circuit uses Peltier elements as heat exchangers. A controller can also be used to provide a closed-loop temperature control with the aid of a platinum electronic temperature sensor integrated into its control circuit.

The measurement chamber 104 can be provided with a simple flap mechanism, through which the sensor carriers 110 can be transported on the take in/out mechanism 118. The flap mechanism could be held closed by a spring. The transport of the sensor carriers 110 is effected by the take in/out mechanism 118 which is mounted to a linear guide and moved, for example, by a stepper motor using a toothed belt. The take in/out mechanism 118 moves and pushes the flap open which is considerably simpler than using complicated baffle mechanisms. The linear guide of the take in/out mechanism 118 terminates in the range of action of the vertically movable gripper 113, which is part of the internal plate handling system 112.

The preferred gripper 113 has multiple transfer/holding positions within the measurement chamber 104 including: (1) the barcode reading position; (2) the take in/out mechanism 118; (3) the measurement nest 302 on the x-y moveable table 122; and (4) the temperature compensation bodies 128 on the different levels of the plate carousel 130. The gripper 113 can reach all of these positions by making one single movement along a vertical linear guide which ensures a very quick transfer of the temperature compensated sensor carriers 110 from the plate carousel 130 to the x-y moveable table 122 and this prevents the occurrence of unnecessary changes in the temperature of the sensor carriers 110. The barcode reading position is preferably located at a height between the x-y moveable table 122 and the lowest level of the plate carousel 130. The barcode reader should be mounted at an orientation that is relative to the sensor carrier 110 while it is secured by the gripper 113.

The plate carousel 130 includes a plurality of equilibration sites 126 (on which are secured the temperature compensation bodies 128) which can be connected by thin, fiber-reinforced plastic rods to a central column 132, for example. The central column 132 is provided with a rotation bearing and is moved, for example, by a stepper motor using a toothed belt. The levels and the allocation of space between the equilibration sites 126 (including the height of a sensor carrier 110 and the temperature compensation bodies 128) on one level are selected such that the gripper 113 can move between them. Thus, with respect to the rotation of the plate carousel 130, there is a plurality of, in this example, four positions in which the gripper 113 can be vertically displaced. The different positions of the plate carousel 130 and of the gripper 113 are monitored by combinations of position sensors and incremental angle sensors that are associated with the various stepper motors.

If desired, the equilibration sites 126/temperature compensation bodies 128 can have: (1) conical positioning elements which function to help align the sensor carriers 110; and (2) suitable recesses which provide the free space for the required movement of the gripper 113. The gripper 113 itself can be embodied as a form-locking three-finger gripper 113 which grips the bottom of the sensor carrier 110. A force-locking grip could also be used but it is generally considered as not being so safe and as being less convenient for transferring the sensor carriers 110 to the measurement position.

Figure 1A:
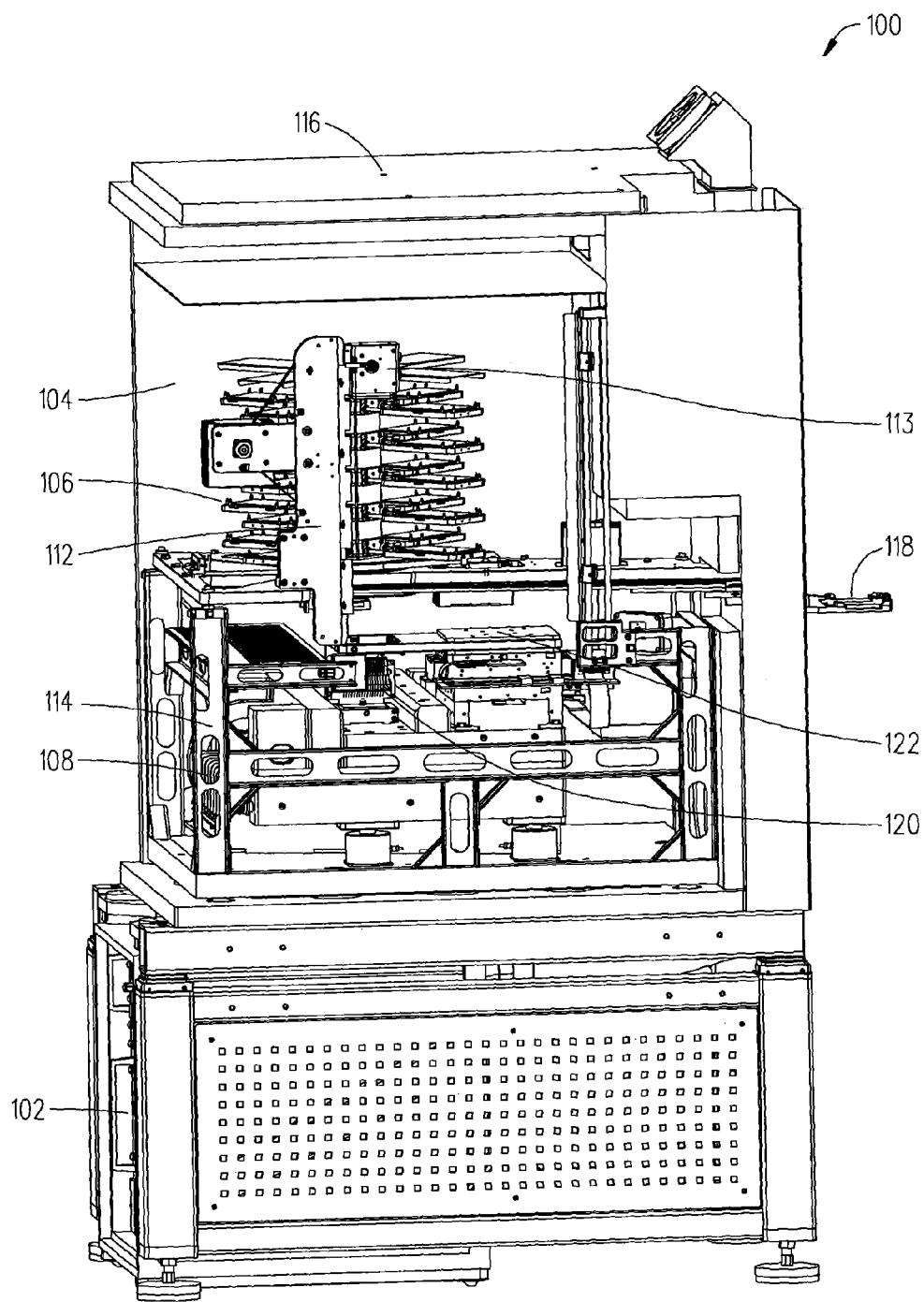
FIGS. 1A-1F are various diagrams illustrating different views of a screening system in accordance with the present invention.
Figure 1B:
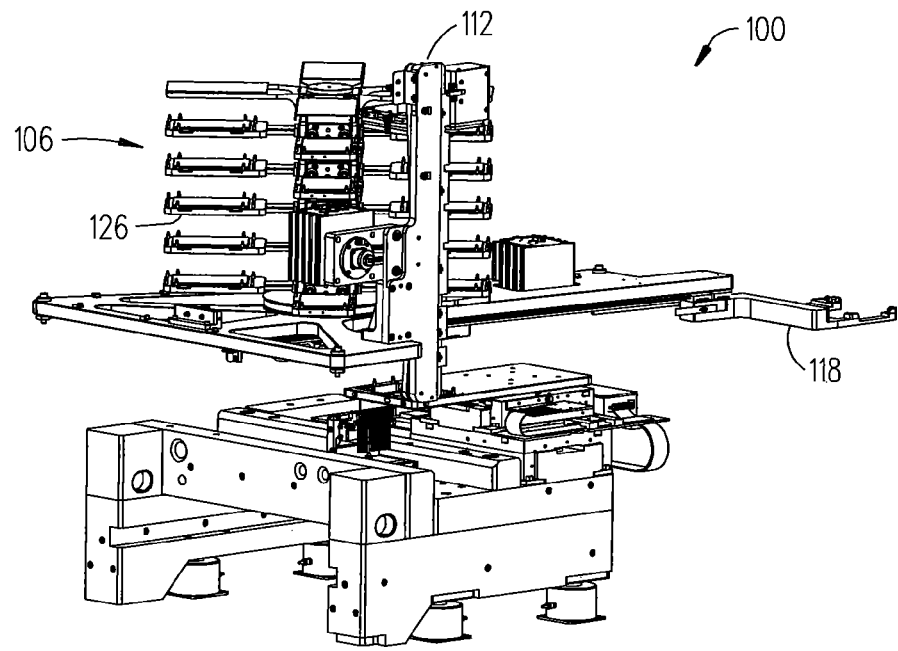
Figure 1C:
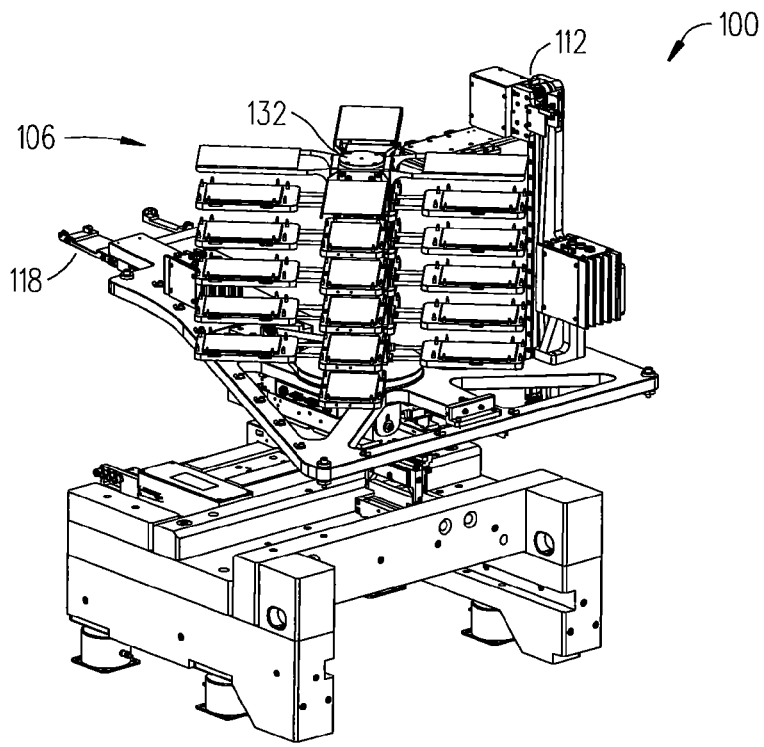
Figure 1D:
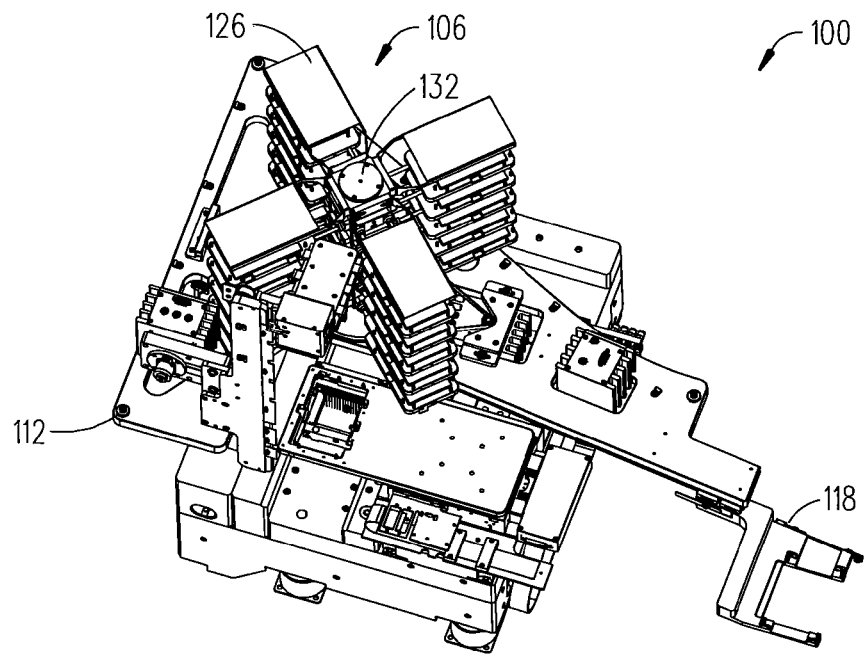
Figure 1E:
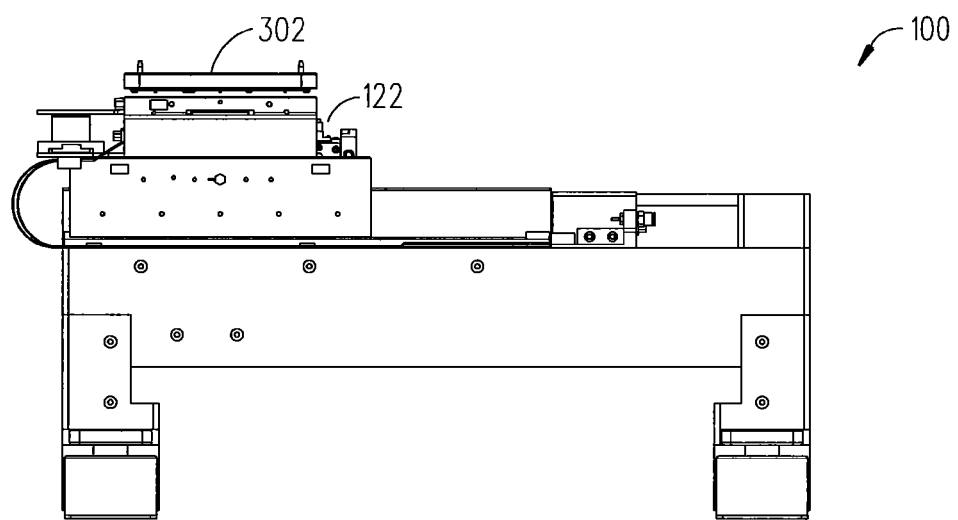
Figure 1F:
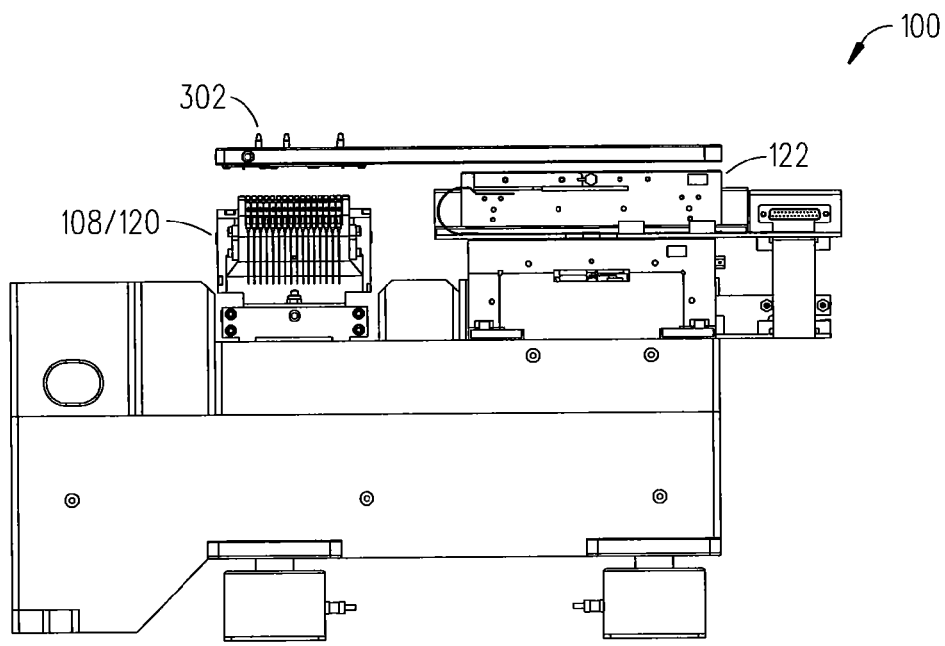
Figure 2:
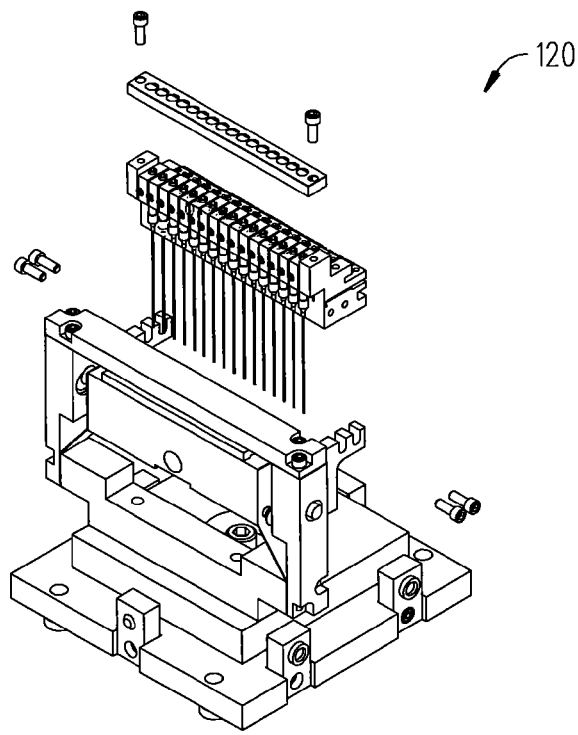
FIG. 2 is a diagram illustrating an exemplary measurement device which can be used within the screening system in accordance with the present invention.
Figure 3:
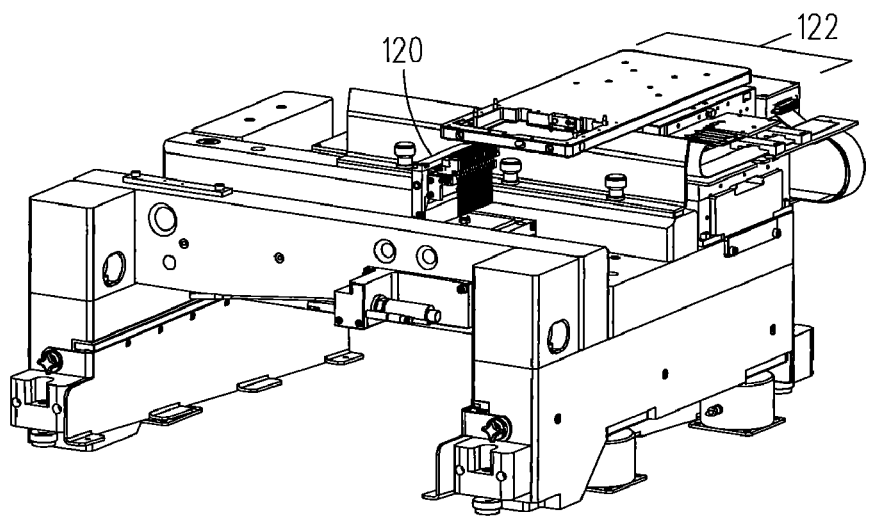
FIG. 3 is a diagram illustrating an exemplary x-y moveable table which can be used within the screening system in accordance with the present invention.

In the lowermost position, corresponding to the range of movement of the gripper 113, there is the measurement nest 302 of the x-y moveable table 122 (which is supported on air bearings) (see FIG. 3). This measurement nest 302 (which can have the form of a temperature compensation body 128) is designed such it has recesses to make room for the fingers of the gripper 113. In addition, the measurement nest 302 can have spring/ball elements, which align the sensor carrier 110 in a defined manner relative to the frame. Typically, the gripper 113 usually pushes the sensor carrier 110 in the direction of the A1 corner of the measurement nest 302. Then, the gripper 113 applies a vertically directed force on the sensor carrier 110 to overcome the resilient force of the spring/ball elements and ensure a defined support of the sensor carrier 110 in the measurement nest 302.

10. Measurement System 108 for Grating Sensors

Figure 16:
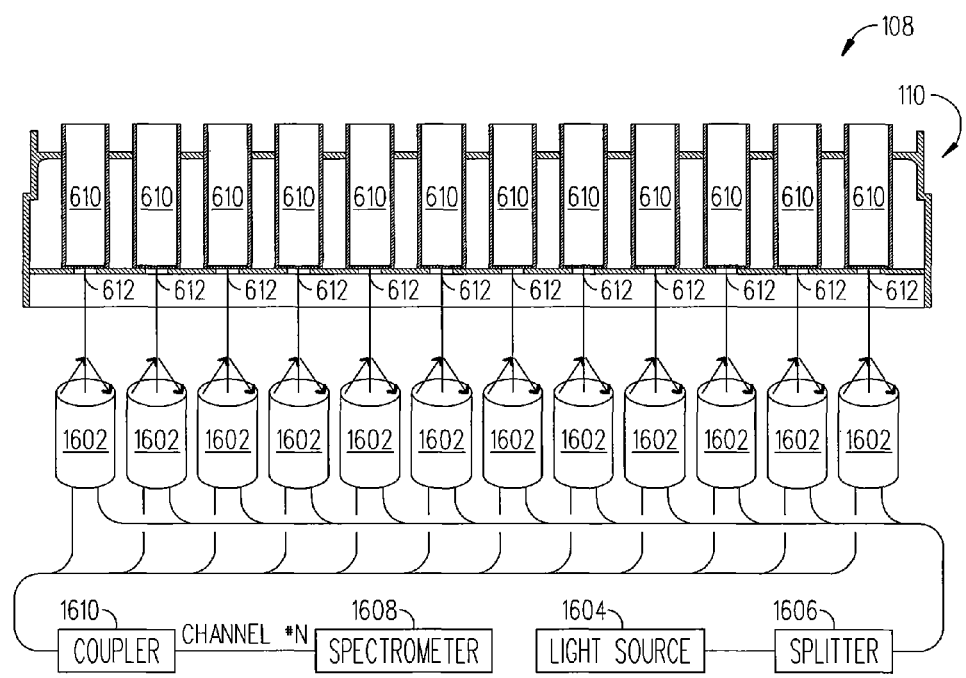
FIG. 16 is a diagram illustrating an exemplary measurement system that can be used by the screening system to interrogate RWG biosensors in accordance with the present invention.
Figure 17A:
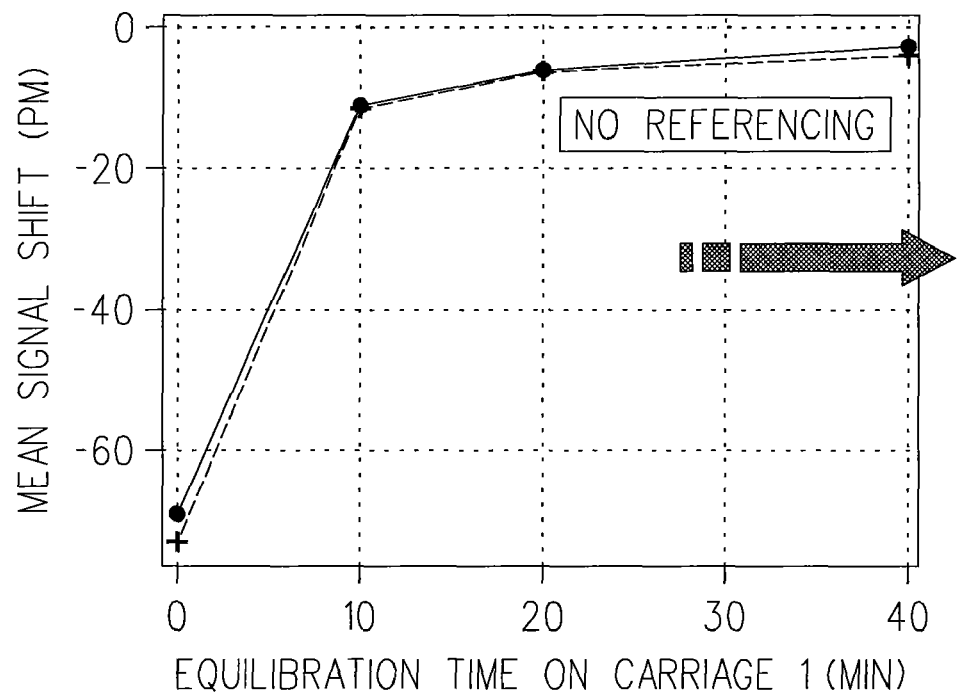
FIGS. 17A-17D are graphs which illustrate the temperature development over time within an exemplary microplate without using a temperature compensation body (see 0 minute) and with using a temperature compensation body (see time after 0 minutes) that helps indicate an advantage of using the screening system in accordance with the present invention.
Figure 17B:
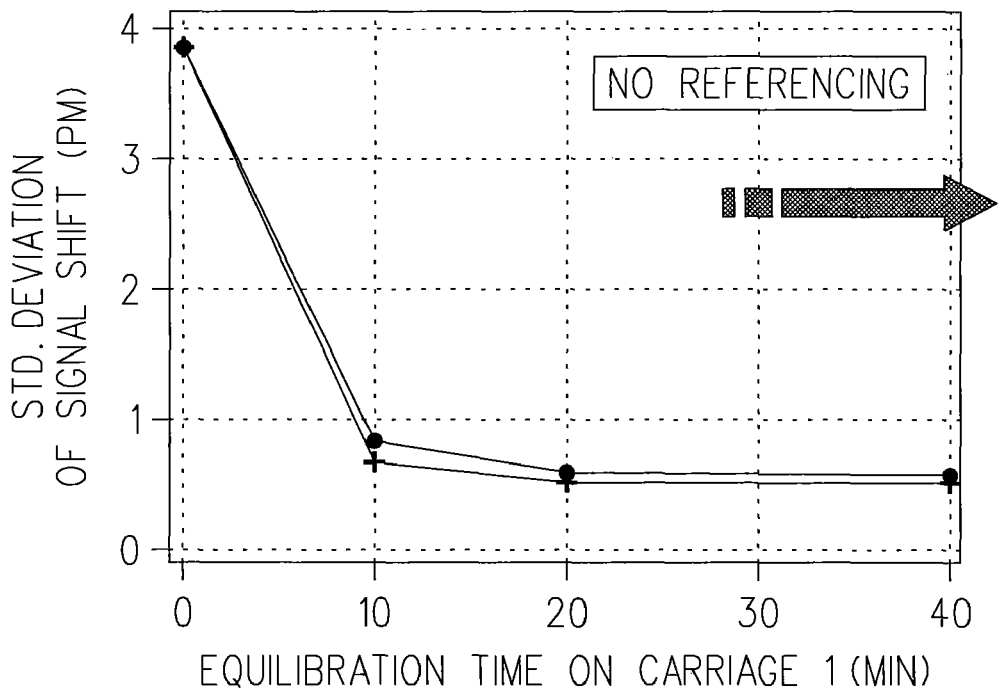
Figure 17C:
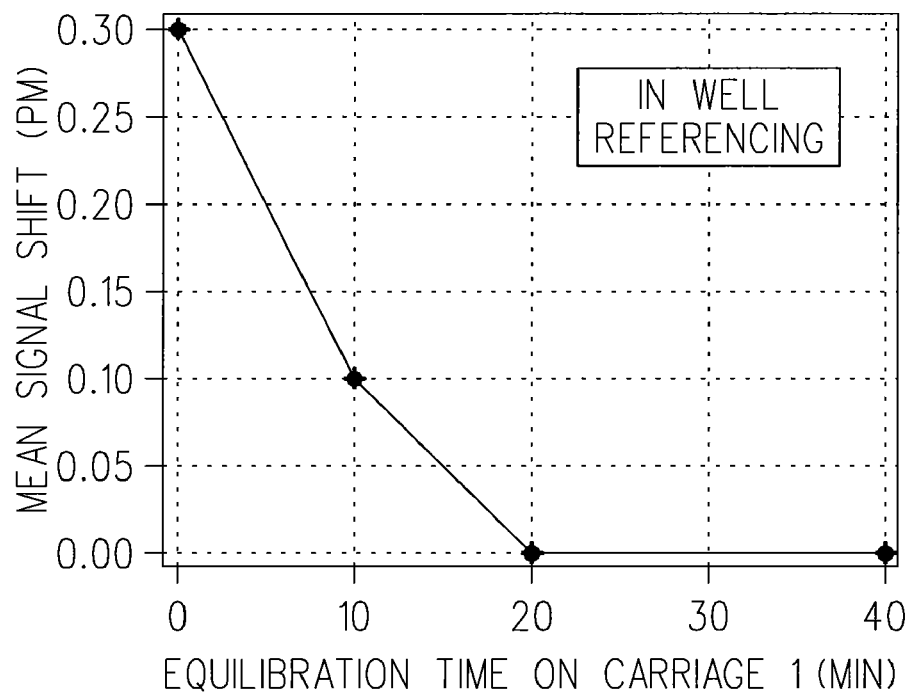
Figure 17D:
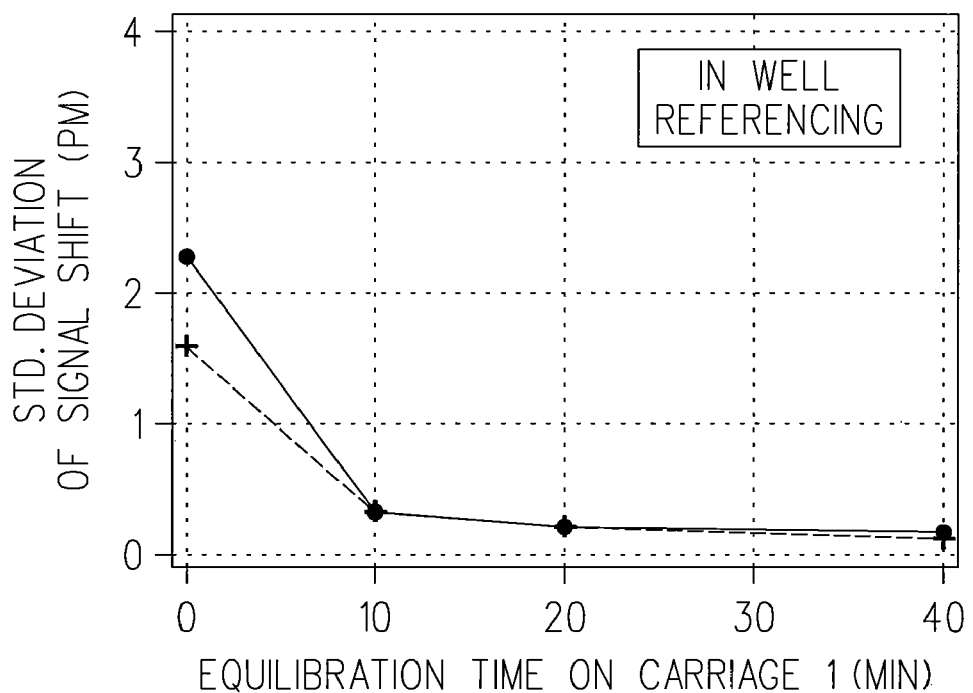
Figure 18:
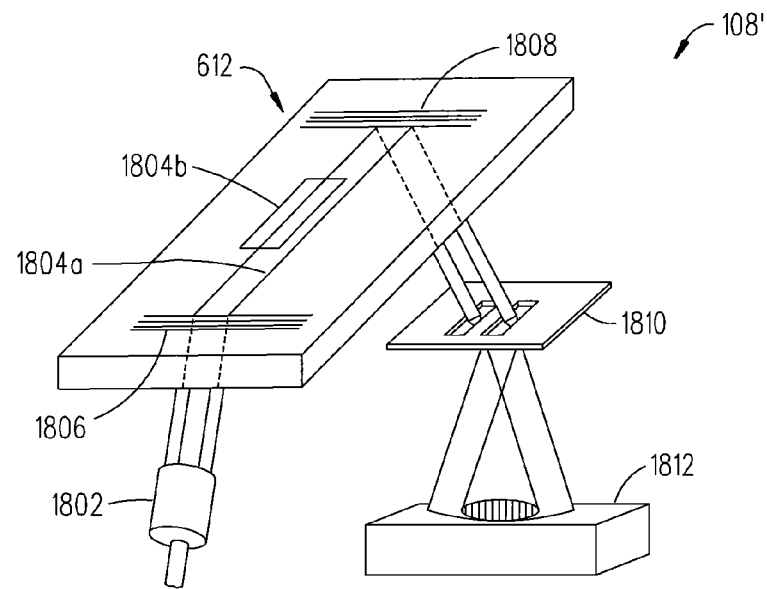
FIG. 18 is a diagram illustrating an exemplary measurement system that can be used by the screening system to interrogate waveguide interferometers in accordance with the present invention.
Figure 19:
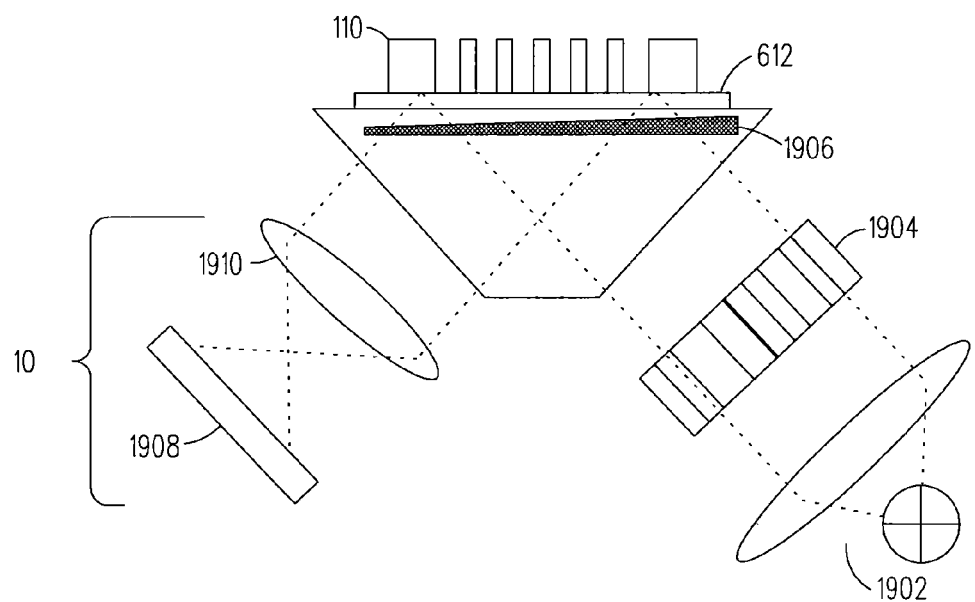
FIG. 19 is a diagram illustrating an exemplary measurement system that can be used by the screening system to interrogate RIFS transducers/sensors in accordance with the present invention.

As shown in FIG. 16, this particular measurement device 108 has a plurality of serially arranged fiber-optical scanning elements 1602, a common semi-conductor light source 1604 (with splitter 1606), and one opto-electronic spectrometer 1608 (with coupler 1610) per measurement channel. Typically, the sensor carrier 110 is scanned in the longitudinal (x) direction by moving the x-y moveable table 122. Then, the scanning track is changed at right angles, so that each biosensor 612 in each well 610 can be measured along a (y) direction in one or more places. The scanning operation itself is synchronized by a path measurement system, which is part of the x-y moveable table 122. This path measurement system has a sub-µm path resolution. For a more detailed discussion about an exemplary measurement system 108 reference is made to U.S. Pat. No. 6,829,073 (the contents of which are incorporated by reference herein).

Each sensor carrier 110 is typically measured at least twice. A first measurement is effected without binding molecules and is referred to as a baseline measurement. The second measurement is effected with the binding molecule and is referred to as an end-point measurement. For the baseline measurement, the sensor carrier 110 is charged with a buffer outside the screening system 100 and is incubated at room temperature for a sufficient time. Then, the sensor carrier 110 is placed on the transport carriage 118 (take in/out mechanism 118) and transported into the screening system 100. Thereafter, the temperature of the sensor carrier 110 is determined, the barcode is read, and the sensor carrier 110 is placed by the handling system 112 onto a computer-addressed temperature compensation body 128 in the plate carousel 130 (see FIGS. 1A-1F). This operation is repeated until the first of the sensor carriers 110 has been on the temperature compensation bodies 128 for a sufficiently long time. That is, until the temperature equilibration of the first sensor carrier 110 is complete such that the gripper 113 can deposit this sensor carrier 110 onto the measurement nest 302 of the x-y moveable table 122 which is then moved over to the measurement device 108. This sensor carrier 110 is scanned to obtain one or more readings of the so-called baseline measurement, and then it is transported out of the measurement chamber 104. This operation is repeated until the last sensor carrier 110 of this particular series of sensor carriers 110 has been baseline measured.

Once, the sensor carriers 110 have been baseline measured, they are charged with binding molecules by an external liquid handling unit outside of the screening system 100 and are incubated for a sufficiently long time. After this incubation step, the sensor carriers 110 are transported into the screening system 100 a second time, equilibrated and measured (end-point measurement). By offsetting the two readings against each other, the parameters of the binding behavior of the molecules per well in the sensor carriers 110 can be obtained. The overlapping operation of storing the sensor carriers 110 for baseline and end-point measurements on top of the temperature compensation bodies for the purpose of equilibration in the screening system 100 can be enabled by suitable software, e.g. a scheduler. To this end, it is important that the equilibration times for both steps of the measurements are not below a predetermined minimum threshold.

11. Temperature Equilibration in Microplates

The temperature development over time in an exemplary microplate 600 (sensor carrier 110) without using a temperature compensation body 128 (carriage 128) and with using a temperature compensation body 128 (carriage 128) is shown in FIGS. 17A-17D (where the '0' time in the graphs indicates the point when the microplate 110 is first placed on top of the temperature compensation body 128). If a constant temperature of approximately 0.2 K is required over the entire microplate 110, then these readings show that this value is reached with the aid of the temperature compensation body 128 after approximately 20 minutes. This time is the minimum equilibration time and knowing this time allows one to determine the required storage capacity of the plate carousel 130. It is clear that without the use of a temperature compensation body 128 then a considerably greater storage capacity would be required on the plate carousel 130. If a greater storage capacity is required then this also means that increasingly long paths are needed to transport the microplates 110, which in turn takes more time and may even change the equilibration-generated temperature profile on the microplates 110. Thus, the equilibration time of the microplates 110 spent on the temperature compensation bodies 128 directly affects the required storage capacity on the plate carousel 130 and also the sensitivity of the measurement analyses.

12. Measurement Device 108 for Waveguide Interferometers

As described above, a sensor carrier 110 with waveguide interferometers 612 located therein could also be transferred to a measurement nest 302 on the x-y moveable table 122 which can then perform a scanning movement over the measurement device 108. In this case, the measurement device 108 would be similar to the Fraunhofer measurement device 108' shown in FIG. 18. The Fraunhofer measurement device 108' has several beam splitters 1802 (one shown) which operate in parallel to couple light into each well and in particular into each of the two interferometer arms 1804a and 1804b of the waveguide interferometers 612 with the help of a coupling-in grating 1806 (see also FIG. 11B). After, the light passes through these two sensor regions 1804a and 1804b, it is coupled out by a coupling-out grating 1808 (per well) and passed through a double slit 1810 and imaged in a superimposed manner onto a CCD sensor 1812. The interferogram thus generated represents the difference in refractive index between the two waveguides 1804a and 1804b in the waveguide interferometer 612.

13. Measurement Device 108 for RIFS Transducer/Sensor

As described above, a sensor carrier 110 with RIFS transducers/sensors 612 located therein could also be transferred to a measurement nest 302 on the x-y moveable table 122 which can perform a scanning movement over the measurement device 108. In this case, the measurement device 108 would be similar to the ZEISS measurement device 108" shown in FIG. 19. This particular measurement device 108" includes an image-generating white-light interferometer 1902 and a monochromater 1904 which directs light through a wedge-shaped end window 1906 that is shown located below the RIFS transducer/sensor 612. Then, a CCD sensor 1908 would receive via a lens 1910 the light reflected from RIFS transducer/sensor 612.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A screening system, comprising:
a temperature equilibration system which includes a temperature compensation body on which a sensor carrier is stored for a predetermined amount of time to ensure there is a substantially constant temperature gradient across at least a portion of the sensor carrier, wherein the sensor carrier has multi-dimensionally arranged, temperature-compensated or temperature-compensatable optical sensors; and
a measurement system which interrogates one or more of the optical sensors located within the sensor carrier when there is still the substantially constant temperature gradient present across at least a portion of the sensor carrier.

2. The screening system of claim 1, wherein said temperature compensation body has a bottom which is configured to match a bottom of the sensor carrier and is also configured to not damage the sensors within the sensor carrier.

3. The screening system of claim 1, further comprising a temperature sensor which measures an incoming temperature of the sensor carrier and then the measured incoming temperature is used to calculate the predetermined amount of time that the sensor carrier needs to be placed on said temperature compensation body to ensure there is a substantially constant temperature gradient across the at least a portion of the sensor carrier.

* * * * *